(12) United States Patent
Dyballa et al.

(10) Patent No.: US 9,982,001 B2
(45) Date of Patent: *May 29, 2018

(54) BISPHOSPHITES HAVING AN UNSYMMETRIC CENTRAL BIARYL UNIT

(71) Applicants: Katrin Marie Dyballa, Recklinghausen (DE); Robert Franke, Marl (DE); Dirk Fridag, Haltern am See (DE); Armin Börner, Rostock (DE); Detlef Selent, Rostock (DE)

(72) Inventors: Katrin Marie Dyballa, Recklinghausen (DE); Robert Franke, Marl (DE); Dirk Fridag, Haltern am See (DE); Armin Börner, Rostock (DE); Detlef Selent, Rostock (DE)

(73) Assignee: EVONIK DEGUSSA GMBH, Essen (DE)

( * ) Notice: Subject to any disclaimer, the term of this patent is extended or adjusted under 35 U.S.C. 154(b) by 58 days.

This patent is subject to a terminal disclaimer.

(21) Appl. No.: 14/958,143

(22) Filed: Dec. 3, 2015

(65) Prior Publication Data

US 2016/0159839 A1    Jun. 9, 2016

(30) Foreign Application Priority Data

Dec. 4, 2014  (EP) .................................. 14196178

(51) Int. Cl.
| | |
|---|---|
| *C07F 9/6574* | (2006.01) |
| *C07C 45/50* | (2006.01) |
| *C07F 15/00* | (2006.01) |
| *C07F 15/06* | (2006.01) |

(52) U.S. Cl.
CPC .......... *C07F 9/65744* (2013.01); *C07C 45/50* (2013.01); *C07F 9/65746* (2013.01); *C07F 15/0033* (2013.01); *C07F 15/0046* (2013.01); *C07F 15/0073* (2013.01); *C07F 15/06* (2013.01)

(58) Field of Classification Search
CPC .............. C07F 9/65744; C07F 15/0033; C07F 15/0046
See application file for complete search history.

(56) References Cited

U.S. PATENT DOCUMENTS

| 4,694,109 A | 9/1987 | Devon et al. |
| 4,879,416 A | 11/1989 | Puckette et al. |
| 6,570,033 B2 | 5/2003 | Röttger et al. |
| 6,818,770 B2 | 11/2004 | Selent et al. |
| 7,009,068 B2 | 3/2006 | Schmutzler et al. |
| 7,161,020 B2 | 1/2007 | Selent et al. |
| 7,361,786 B2 | 4/2008 | Boerner et al. |
| 7,589,215 B2 | 9/2009 | Boerner et al. |
| 7,767,861 B2 | 8/2010 | Ortmann et al. |
| 7,834,215 B2 | 11/2010 | Holz et al. |
| 8,003,816 B2 | 8/2011 | Selent et al. |
| 8,729,287 B2 | 5/2014 | Fridag et al. |
| 9,127,030 B2 | 9/2015 | Kreidler et al. |
| 2005/0209455 A1 | 9/2005 | Boerner et al. |
| 2013/0317246 A1 | 11/2013 | Kriedler et al. |
| 2015/0266008 A1 | 9/2015 | Christiansen et al. |
| 2015/0274627 A1 | 10/2015 | Christiansen et al. |
| 2015/0290633 A1 | 10/2015 | Christiansen et al. |
| 2015/0336988 A1 | 11/2015 | Dyballa et al. |
| 2015/0336989 A1 | 11/2015 | Dyballa et al. |
| 2016/0159840 A1* | 6/2016 | Dyballa ................ B01J 31/185 558/78 |

FOREIGN PATENT DOCUMENTS

| DE | 102006058682 | 6/2008 |
| DE | 102008043584 | 5/2010 |
| EP | 0 900 187 B1 | 9/2002 |
| JP | H10-130190 | 5/1998 |
| WO | 95/30680 | 11/1995 |
| WO | 02/00670 A1 | 1/2002 |
| WO | 03/016322 A1 | 2/2003 |
| WO | 2005/049629 A1 | 6/2005 |
| WO | 2006/045388 A1 | 5/2006 |
| WO | 2008/071508 | 6/2008 |
| WO | 2014/056735 A1 | 4/2014 |

OTHER PUBLICATIONS

Detlef; Organometallics; 2011, 30, 4509-4514.*
Franke et al. Applied Hydroformylation. American Chemical Society, ACS Publications, Chemical Reviews, 2012. pp. 5675-5732.
Cornils et al. Applied Homogeneous Catalysis with Organometallic Compounds, vol. 1 & 2, VCH, Weinheim, New York, 1996. Forward, Preface and Table of Contents provided.
Search Report for European Patent Application No. 15173831.7 dated Oct. 23, 2015 (11 pages).
Search Report for European Patent Application No. 15173827.5 dated Oct. 26, 2015 (13 pages).
Detlef Selent et al. A New Diphosphite Promoting Highly Regioselective Rhodium-Catalyzed Hydroformylation. Organometallics. ACS Publications. American Chemical Society. 2011. pp. 4509-4514.
Search Report for European Patent Application No. 15173833.3 dated Nov. 3, 2015.
Sedo, Yoko et al. "Preparation of aldehydes by hydroformylation of olefins", Database CA [Online] Chemical Abstracts Service, Columbus OH, US. XP002746393; database accession No. 1998:314684.
van Leeuwen, Piet W. N. M. "Chapter 9: Catalyst preparation and decomposition" in Rhodium Catalyzed Hydroformylation edited by P. W. N. M. van Leeuwen and C. Claver, Kluwer, Dordrecht, 2000, pp. 233-251.
Elsler, Bernd, et al. Metal-and Reagent-Free High-Selectivity Anodic Cross-Coupling of Phenols. Angew. Chem., 2014. pp. 5210-5213.
Wiese, Klaus-Diether, et al. Hydroformylation. Top Organomet Chem. 2006, vol. 18, pp. 1-33.

* cited by examiner

*Primary Examiner* — Pancham Bakshi
(74) *Attorney, Agent, or Firm* — Smith, Gambrell & Russell, LLP

(57) ABSTRACT

Bisphosphites having an unsymmetric central biaryl unit.

15 Claims, 1 Drawing Sheet

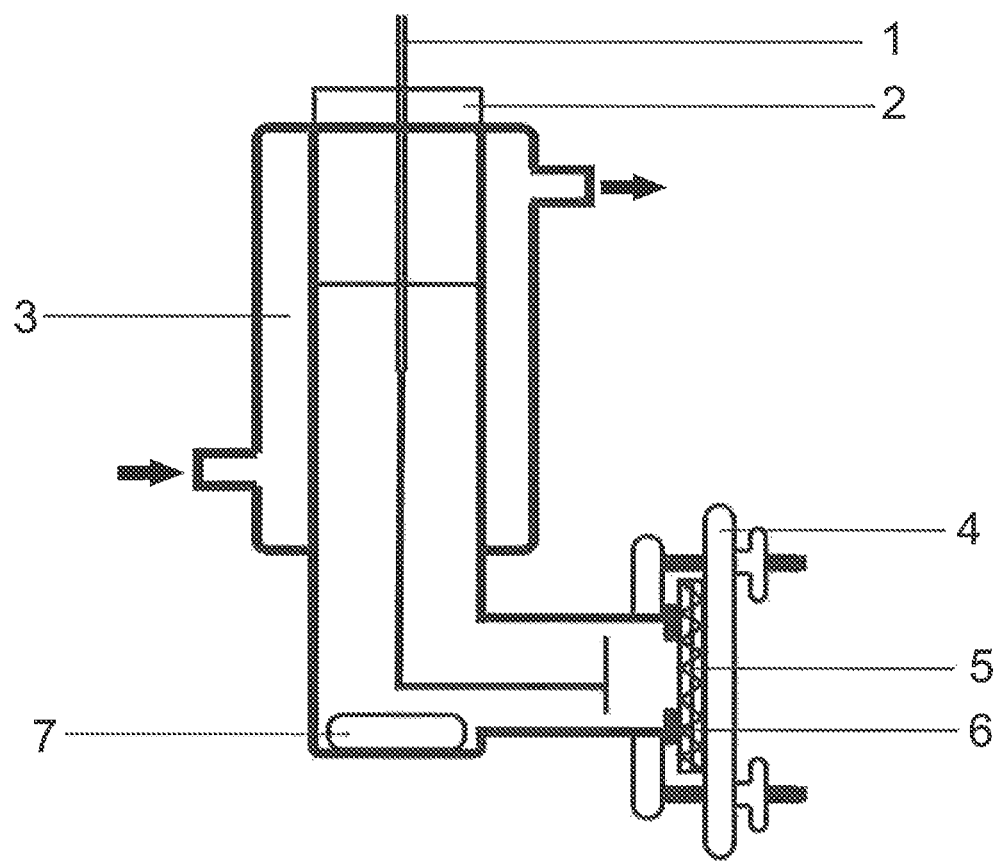

BISPHOSPHITES HAVING AN UNSYMMETRIC CENTRAL BIARYL UNIT

The invention relates to bisphosphites having an unsymmetric central biaryl unit. In addition, the use thereof as ligands in hydroformylation.

A bisphosphite has a central unit, called the backbone, and two outer units bonded to the central unit via the phosphorus atom.

The central biaryl units of the invention have, for example, a phenyl-phenyl unit or a naphthyl-phenyl unit.

The reactions between olefin compounds, carbon monoxide and hydrogen in the presence of a catalyst to give the aldehydes comprising one additional carbon atom are known as hydroformylation or oxo synthesis. In these reactions, compounds of the transition metals of group VIII of the periodic table of the elements are frequently employed as catalysts. Known ligands include, for example, compounds of the phosphine, phosphite and phosphonite classes each comprising trivalent phosphorus $P^{III}$. A good overview of the state of the hydroformylation of olefins can be found in B. CORNILS, W. A. HERRMANN, "Applied Homogeneous Catalysis with Organometallic Compounds", vol. 1 & 2, VCH, Weinheim, N.Y., 1996 or R. Franke, D. Selent, A. Börner, "Applied Hydroformylation", Chem. Rev., 2012, DOI:10.1021/cr3001803.

Every catalytically active composition has its specific benefits. According to the feedstock and target product, therefore, different catalytically active compositions are used.

U.S. Pat. Nos. 4,694,109 and 4,879,416 describe bisphosphine ligands and use thereof in the hydroformylation of olefins at low synthesis gas pressures. Particularly in the case of hydroformylation of propene, ligands of this type achieve high activities and high n/i selectivities (n/i=the ratio of linear aldehyde (=n) to branched (=iso) aldehyde). WO 95/30680 discloses bidentate phosphine ligands and the use thereof in catalysis, including in hydroformylation reactions.

DE 10 2006 058 682 A1 discloses bisphosphites having a symmetric central unit (Y). This may be selected from the formulae IIa to IId or III disclosed in DE 10 2006 058 682 A1 paragraph [0022].

Even though a multitude of ligands and the use thereof in rhodium-catalysed hydroformylation are known, it is desirable to develop new ligands having improved properties.

The problem addressed by the invention was that of providing bisphosphites having advantageous properties in hydroformylation compared to the known bisphosphites. The problem addressed was more particularly that of providing novel ligands which, as well as a good yield, also generate a high n selectivity for the corresponding aldehydes in the conversion of terminal olefins and which likewise have satisfactory n/i selectivities in the hydroformylation of internal olefins. As well as a good yield, a good selectivity is thus additionally also to be achieved.

The problem is solved by a compound according to Claim 1.

Compound having one of the four general structures I to IV:

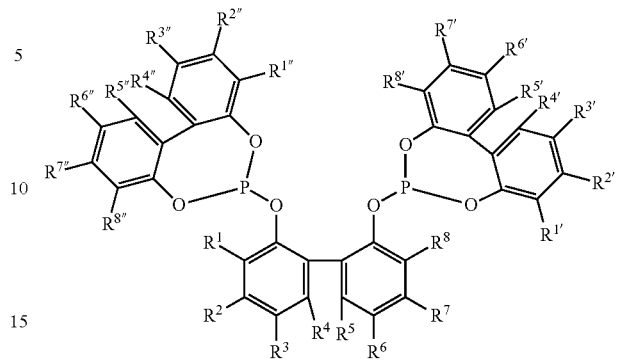
(I)

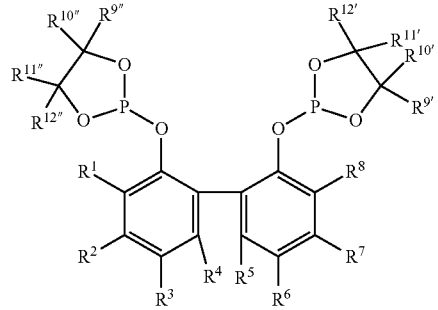
(II)

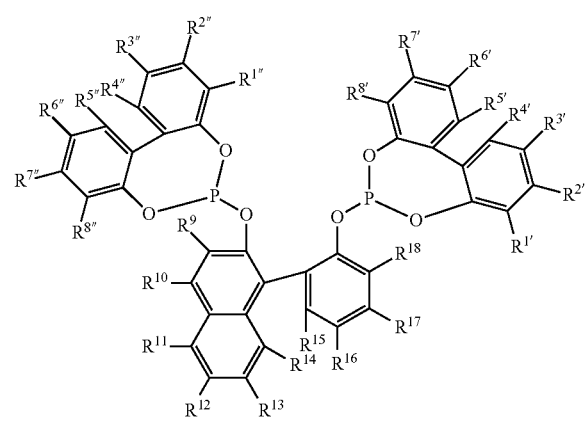
(III)

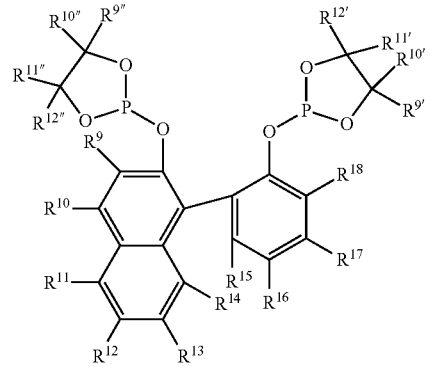
(IV)

where
$R^1, R^2, R^3, R^4, R^5, R^6, R^7, R^8, R^9, R^{10}, R^{11}, R^{12}, R^{13}, R^{14}, R^{15}, R^{16}, R^{17}, R^{18}$ are selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—

$(C_1-C_{12})$-alkyl, —CO—$(C_6-C_{20})$-aryl, —COOH, —OH, —SO$_3$H, —CN, —NH$_2$, —N[$(C_1-C_{12})$-alkyl]$_2$;

$R^{1'}, R^{2'}, R^{3'}, R^{4'}, R^{5'}, R^{6'}, R^{7'}, R^{8'}, R^{1'''}, R^{2'''}, R^{3'''}, R^{4'''}, R^{5'''}, R^{6'''}, R^{7'''}, R^{8'''}$ are selected from:

—H, —$(C_1-C_{12})$-alkyl, —O—$(C_1-C_{12})$-alkyl, —O—$(C_6-C_{20})$-aryl, —$(C_6-C_{20})$-aryl, —S-alkyl, —S-aryl, halogen, COO—$(C_1-C_{12})$-alkyl, CONH—$(C_1-C_{12})$-alkyl, —CO—$(C_1-C_{12})$-alkyl, —CO—$(C_6-C_{20})$-aryl, —COOH, —OH, —SO$_3$H, —NH$_2$, —N[$(C_1-C_{12})$-alkyl]$_2$;

$R^{9'}, R^{10'}, R^{11'}, R^{12'}, R^{9'''}, R^{10'''}, R^{11'''}, R^{12'''}$ are selected from:
—H, —$(C_6-C_{20})$-aryl;

and the two radicals in at least one of the four following radical pairs are not the same radical: $R^1$ and $R^8$, $R^2$ and $R^7$, $R^3$ and $R^6$, $R^4$ and $R^5$;

where the alkyl and aryl groups mentioned may be substituted.

The feature "and the two radicals in at least one of the four following radical pairs are not the same radical: $R^1$ and $R^8$, $R^2$ and $R^7$, $R^3$ and $R^6$, $R^4$ and $R^5$" expresses the fact that this is an unsymmetric biaryl. The two aromatic systems cannot be reflected onto one another by a mirror plane lying between them.

The following radical pairs are permitted, for example:
$R^1 \neq R^8, R^2 = R^7, R^3 = R^6, R^4 = R^5$;
$R^1 = R^8, R^2 = R^7, R^3 \neq R^6, R^4 = R^5$.

But also radical pairs in which more than just one pair is not the same, for example:
$R^1 \neq R^8, R^2 = R^7, R^3 \neq R^6, R^4 = R^5$;
$R^1 \neq R^8, R^2 \neq R^7, R^3 \neq R^6, R^4 = R^5$.

The only case ruled out is that in which all four radical pairs are each the same radical in pairs:
$R^1 = R^8, R^2 = R^7, R^3 = R^6, R^4 = R^5$.

This would be a symmetric biaryl.

$(C_1-C_{12})$-Alkyl and O—$(C_1-C_{12})$-alkyl may each be unsubstituted or substituted by one or more identical or different radicals selected from $(C_3-C_{12})$-cycloalkyl, $(C_3-C_{12})$-heterocycloalkyl, $(C_6-C_{20})$-aryl, fluorine, chlorine, cyano, formyl, acyl and alkoxycarbonyl.

$(C_6-C_{20})$-Aryl and —$(C_6-C_{20})$-aryl-$(C_6-C_{20})$-aryl- may each be unsubstituted or substituted by one or more identical or different radicals selected from:

—H, —$(C_1-C_{12})$-alkyl, —O—$(C_1-C_{12})$-alkyl, —O—$(C_6-C_{20})$-aryl, —$(C_6-C_{20})$-aryl, -halogen (such as Cl, F, Br, I), —COO—$(C_1-C_{12})$-alkyl, —CONH—$(C_1-C_{12})$-alkyl, —$(C_6-C_{20})$aryl-CON[$(C_1-C_{12})$-alkyl]$_2$, —CO—$(C_1-C_{12})$-alkyl, —CO—$(C_6-C_{20})$-aryl, —COOH, —OH, —SO$_3$H, —SO$_3$Na, —NO$_2$, —CN, —NH$_2$, —N[$(C_1-C_{12})$-alkyl]$_2$.

In the context of the invention, the expression "—$(C_1-C_{12})$-alkyl" encompasses straight-chain and branched alkyl groups. Preferably, these groups are unsubstituted straight-chain or branched —$(C_1-C_8)$-alkyl groups and most preferably —$(C_1-C_6)$-alkyl groups. Examples of —$(C_1-C_{12})$-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression "—$(C_1-C_{12})$-alkyl" also apply to the alkyl groups in —O—$(C_1-C_{12})$-alkyl, i.e. in —$(C_1-C_{12})$-alkoxy. Preferably, these groups are unsubstituted straight-chain or branched —$(C_1-C_6)$-alkoxy groups.

Substituted —$(C_1-C_{12})$-alkyl groups and substituted —$(C_1-C_{12})$-alkoxy groups may have one or more substituents, depending on their chain length. The substituents are preferably each independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl and alkoxycarbonyl.

The expression "—$(C_3-C_{12})$-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl and adamantyl.

One example of a substituted cycloalkyl would be menthyl.

The expression "—$(C_3-C_{12})$-heterocycloalkyl groups", in the context of the present invention, encompasses nonaromatic saturated or partly unsaturated cycloaliphatic groups having 3 to 12, especially 5 to 12, carbon atoms. The —$(C_3-C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— and —S(=O)—. Examples of —$(C_3-C_{12})$-heterocycloalkyl groups are tetrahydrothiophenyl, tetrahydrofuryl, tetrahydropyranyl and dioxanyl.

In the context of the present invention, the expression "—$(C_6-C_{20})$-aryl and —$(C_6-C_{20})$-aryl-$(C_6-C_{20})$-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —$(C_6-C_{10})$-aryl and —$(C_6-C_{10})$-aryl-$(C_6-C_{10})$-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —$(C_6-C_{20})$-aryl groups and —$(C_6-C_{20})$-aryl-$(C_6-C_{20})$-aryl groups may have one or more (e.g. 1, 2, 3, 4 or 5) substituents, depending on the ring size. These substituents are preferably each independently selected from —H, —$(C_1-C_{12})$-alkyl, —O—$(C_1-C_{12})$-alkyl, —O—$(C_6-C_{20})$-aryl, —$(C_6-C_{20})$-aryl, -halogen (such as Cl, F, Br, I), —COO—$(C_1-C_{12})$-alkyl, —CONH—$(C_1-C_{12})$-alkyl, —$(C_6-C_{20})$-aryl-CON[$(C_1-C_{12})$-alkyl]$_2$, —CO—$(C_1-C_{12})$-alkyl, —CO—$(C_6-C_{20})$-aryl, —COOH, —OH, —SO$_3$H, —SO$_3$Na, —NO$_2$, —CN, —NH$_2$, —N[$(C_1-C_{12})$-alkyl]$_2$.

Substituted —$(C_6-C_{20})$-aryl groups and —$(C_6-C_{20})$-aryl-$(C_6-C_{20})$-aryl groups are preferably substituted —$(C_6-C_{10})$-aryl groups and —$(C_6-C_{10})$-aryl-$(C_6-C_{10})$-aryl groups, especially substituted phenyl or substituted naphthyl or substituted anthracenyl. Substituted —$(C_6-C_{20})$-aryl groups preferably bear one or more, for example 1, 2, 3, 4 or 5, substituents selected from —$(C_1-C_{12})$-alkyl groups, —$(C_1-C_{12})$-alkoxy groups.

In one embodiment, the compound has the general structure (I).

In one embodiment, the compound has the general structure (II).

In one embodiment, the compound has the general structure (III).

In one embodiment, the compound has the general structure (IV).

In one embodiment, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ are selected from:
—H, —($C_1$-$C_{12}$)-alkyl, —O—($C_1$-$C_{12}$)-alkyl, —O—($C_6$-$C_{20}$)-aryl, —S-alkyl, —S-aryl.

In one embodiment, $R^{1\prime}$, $R^{2\prime}$, $R^{3\prime}$, $R^{4\prime}$, $R^{5\prime}$, $R^{6\prime}$, $R^{7\prime}$, $R^{8\prime}$, $R^{1\prime\prime}$, $R^{2\prime\prime}$, $R^{3\prime\prime}$, $R^{4\prime\prime}$, $R^{5\prime\prime}$, $R^{6\prime\prime}$, $R^{7\prime\prime}$, $R^{8\prime\prime}$ are selected from:
—H, —($C_1$-$C_{12}$)-alkyl, —O—($C_1$-$C_{12}$)-alkyl, —O—($C_6$-$C_{20}$)-aryl, —S-alkyl, —S-aryl.

In one embodiment, $R^{9\prime}$, $R^{10\prime}$, $R^{11\prime}$, $R^{12\prime}$, $R^{9\prime\prime}$, $R^{10\prime\prime}$, $R^{11\prime\prime}$, $R^{12\prime\prime}$ are each —($C_6$-$C_{20}$)-aryl.

In one embodiment, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ are selected from:
—H, —($C_1$-$C_{12}$)-alkyl, —O—($C_1$-$C_{12}$)-alkyl.

In one embodiment, $R^{1\prime}$, $R^{2\prime}$, $R^{3\prime}$, $R^{4\prime}$, $R^{5\prime}$, $R^{6\prime}$, $R^{7\prime}$, $R^{8\prime}$, $R^{1\prime\prime}$, $R^{2\prime\prime}$, $R^{3\prime\prime}$, $R^{4\prime\prime}$, $R^{5\prime\prime}$, $R^{6\prime\prime}$, $R^{7\prime\prime}$, $R^{8\prime\prime}$ are selected from:
—H, —($C_1$-$C_{12}$)-alkyl, —O—($C_1$-$C_{12}$)-alkyl.

In one embodiment, $R^{9\prime}$, $R^{10\prime}$, $R^{11\prime}$, $R^{12\prime}$, $R^{9\prime\prime}$, $R^{10\prime\prime}$, $R^{11\prime\prime}$, $R^{12\prime\prime}$ are each phenyl.

In one embodiment, $R^1$ and $R^8$ are not the same radical.

In one embodiment, $R^2$ and $R^7$ are not the same radical.

In one embodiment, $R^3$ and $R^6$ are not the same radical.

In one embodiment, $R^4$ and $R^5$ are not the same radical.

In one embodiment, $R^{9\prime}$, $R^{10\prime}$, $R^{11\prime}$, $R^{12\prime}$, $R^{9\prime\prime}$, $R^{10\prime\prime}$, $R^{11\prime\prime}$, $R^{12\prime\prime}$ are each the same radical.

In one embodiment, $R^{9\prime}$, $R^{10\prime}$, $R^{11\prime}$, $R^{12\prime}$ are the same radical.

In one embodiment, $R^{9\prime\prime}$, $R^{10\prime\prime}$, $R^{11\prime\prime}$, $R^{12\prime\prime}$ are the same radical.

In one embodiment, the two radicals in at least one of the four following radical pairs are not the same radical: $R^{1\prime}$ and $R^{8\prime}$, $R^{2\prime}$ and $R^{7\prime}$, $R^{3\prime}$ and $R^{6\prime}$, $R^{4\prime}$ and $R^{5\prime}$;
and the two radicals in at least one of the four following radical pairs are not the same radical: $R^{1\prime\prime}$ and $R^{8\prime\prime}$, $R^{2\prime\prime}$ and $R^{7\prime\prime}$, $R^{3\prime\prime}$ and $R^{6\prime\prime}$, $R^{4\prime\prime}$ and $R^{5\prime\prime}$.

In one embodiment, the two radicals in at least one of the four following radical pairs are not the same radical: $R^{1\prime}$ and $R^{8\prime}$, $R^{2\prime}$ and $R^{7\prime}$, $R^{3\prime}$ and $R^{6\prime}$, $R^{4\prime}$ and $R^{5\prime}$;
and the two radicals in the four following radical pairs are the same radical: $R^{1\prime\prime}$ and $R^{8\prime\prime}$, $R^{2\prime\prime}$ and $R^{7\prime\prime}$, $R^{3\prime\prime}$ and $R^{6\prime\prime}$, $R^{4\prime\prime}$ and $R^{5\prime\prime}$.

In one embodiment, at least one of the following four radicals differs from the other radicals: $R^{1\prime}$, $R^{8\prime}$, $R^{1\prime\prime}$, $R^{8\prime\prime}$.

In one embodiment, at least one of the following four radicals differs from the other radicals: $R^{2\prime}$, $R^{7\prime}$, $R^{2\prime\prime}$, $R^{7\prime\prime}$.

In one embodiment, at least one of the following four radicals differs from the other radicals: $R^{3\prime}$, $R^{6\prime}$, $R^{3\prime\prime}$, $R^{6\prime\prime}$.

In one embodiment, at least one of the following four radicals differs from the other radicals: $R^{4\prime}$, $R^{5\prime}$, $R^{4\prime\prime}$, $R^{5\prime\prime}$.

In one embodiment, the three radicals in the following groups of three are each the same radical:
$R^1 = R^{1\prime} = R^{1\prime\prime}$,
$R^2 = R^{2\prime} = R^{2\prime\prime}$,
$R^3 = R^{3\prime} = R^{3\prime\prime}$,
$R^4 = R^{4\prime} = R^{4\prime\prime}$,
$R^5 = R^{5\prime} = R^{5\prime\prime}$,
$R^6 = R^{6\prime} = R^{6\prime\prime}$.

In one embodiment, the compound has one of the formulae (1) to (15):

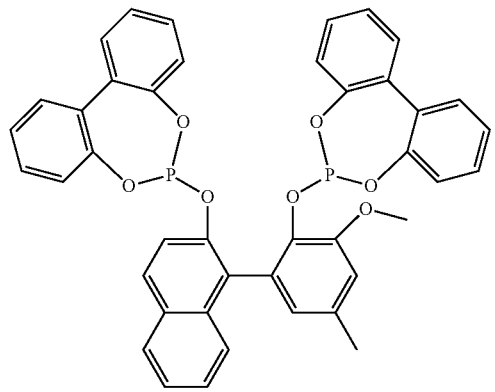

(1)

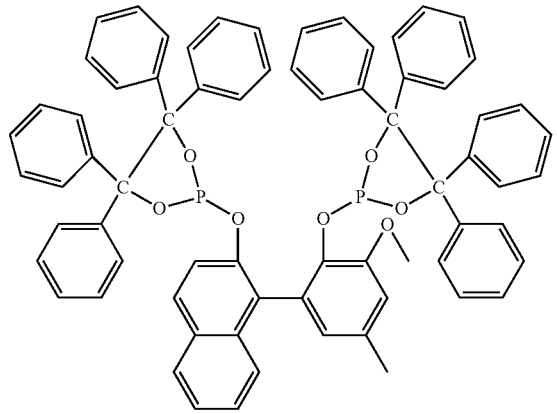

(2)

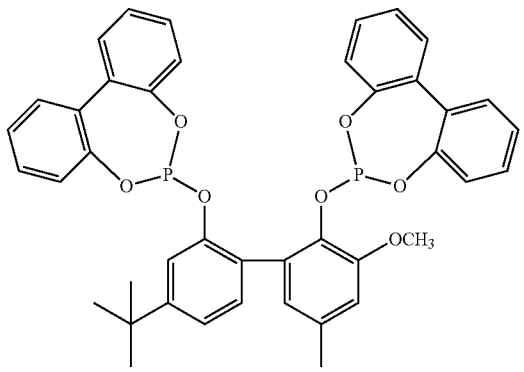

(3)

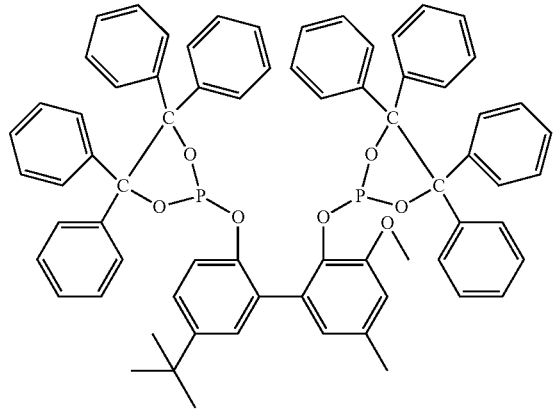

(4)

(5)
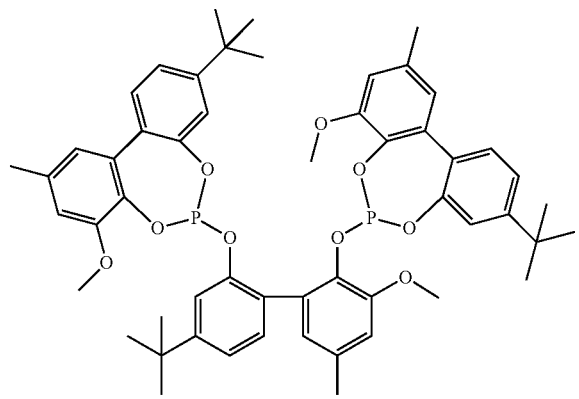
(6)
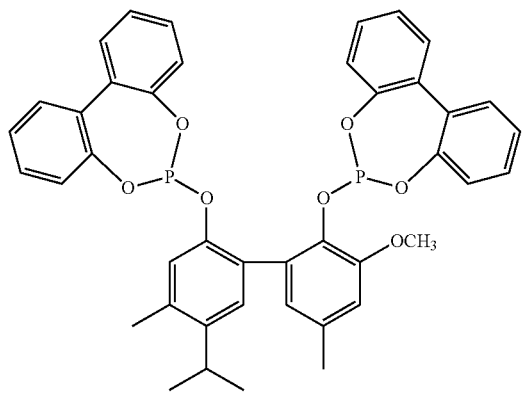
(7)
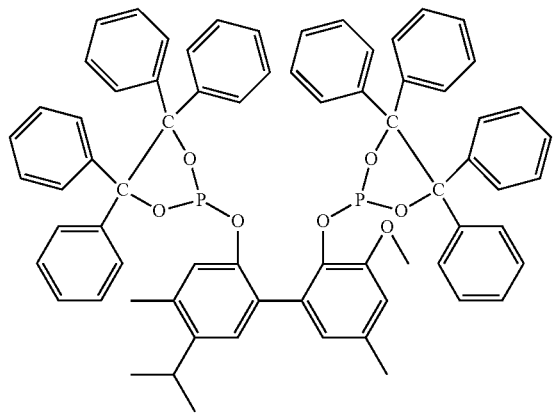
(8)
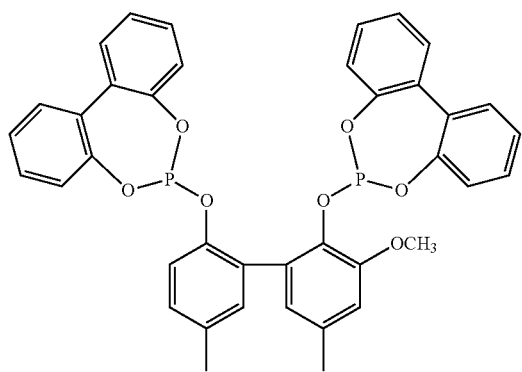
(9)
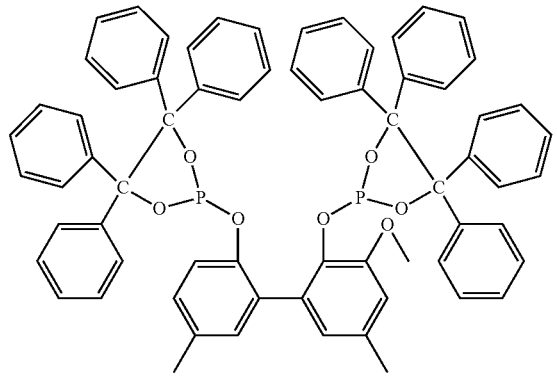
(10)
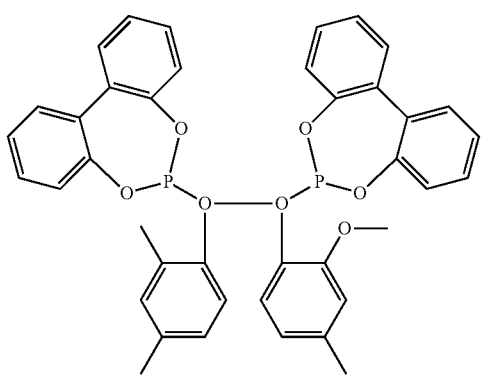
(11)
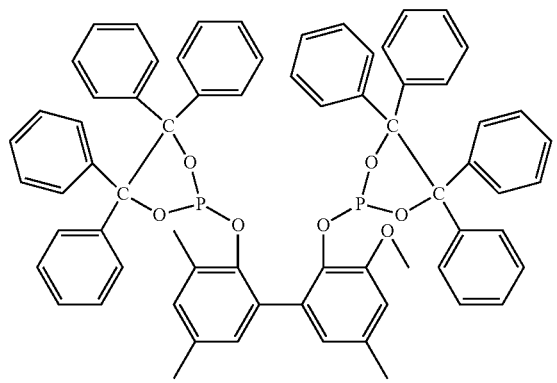
(12)
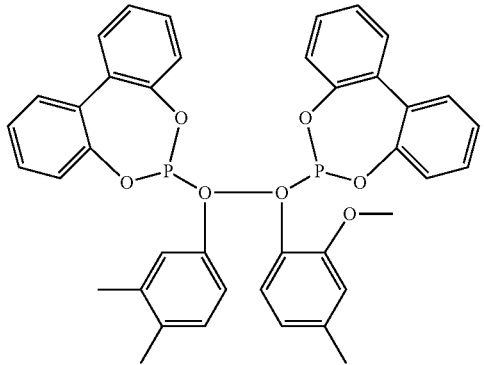

-continued (13)

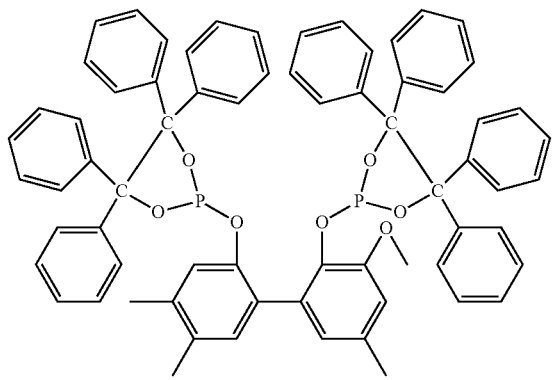

(14)

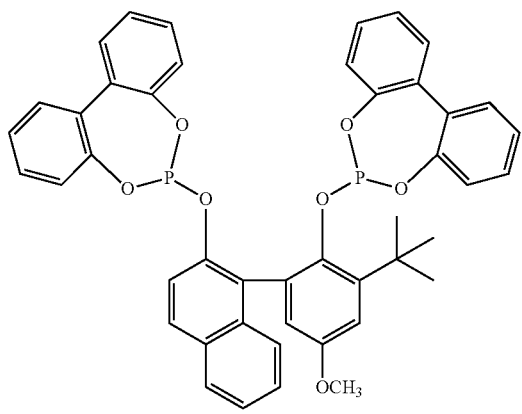

(15)

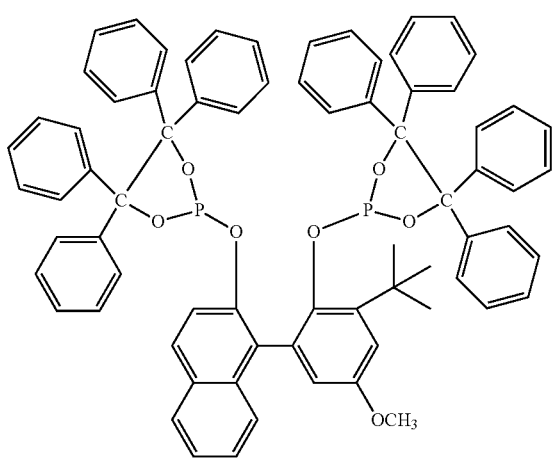

As well as the compounds, also claimed is a complex comprising these compounds.

Complex comprising:
a compound described above,
a metal atom selected from: Rh, Ru, Co, Ir.
In a preferred embodiment, the metal is Rh.

In this regard, see R. Franke, D. Selent, A. Börner, "Applied Hydroformylation", Chem. Rev., 2012, DOI: 10.1021/cr3001803; p. 5688, Scheme 12 "General Method for the Preparation of a P-Modified Rh precatalyst" and references cited therein, and also P. W. N. M. van Leeuwen, in Rhodium Catalyzed Hydroformylation, P. W. N. M. van Leeuwen, C. Claver (eds.), Kluwer, Dordrecht, 2000, inter alia p. 48 ff., p. 233 ff. and references cited therein, and also K. D. Wiese and D. Obst in Top. Organomet. Chem. 2006, 18, 1-13; Springer Verlag Berlin Heidelberg 2006 p. 6 ff. and references cited therein.

Additionally claimed is the use of the compound as ligand in a ligand-metal complex for catalysis of a hydroformylation reaction.

Use of a compound described above in a ligand-metal complex for catalysis of a hydroformylation reaction.

The process in which the compound is used as ligand in a ligand-metal complex for conversion of an olefin to an aldehyde is likewise claimed.

Process comprising the following process steps:
a) initially charging an olefin,
b) adding an above-described complex,
or an above-described compound and a substance including a metal atom selected from: Rh, Ru, Co, Ir,
c) feeding in $H_2$ and CO,
d) heating the reaction mixture, with conversion of the olefin to an aldehyde.

In this process, process steps a) to d) can be effected in any desired sequence.

An excess of ligands can also be used in this case and each ligand is not necessarily present bound in the form of a ligand-metal complex but is present as free ligand in the reaction mixture.

The reaction is conducted under customary conditions.

Preference is given to a temperature of 80° C. to 160° C. and a pressure of 1 bar to 300 bar. Particular preference is given to a temperature of 100° C. to 160° C. and a pressure of 15 bar to 250 bar.

The reactants for the hydroformylation in the process of the invention are olefins or mixtures of olefins, especially monoolefins having 2 to 24, preferably 3 to 16 and more preferably 3 to 12 carbon atoms, having terminal or internal C—C double bonds, for example 1-propene, 1- or 2-pentene, 2-methyl-1-butene, 2-methyl-2-butene, 3-methyl-1-butene, 1-, 2- or 3-hexene, the $C_6$ olefin mixture obtained in the dimerization of propene (dipropene), heptenes, 2- or 3-methyl-1-hexenes, octenes, 2-methylheptenes, 3-methylheptenes, 5-methyl-2-heptene, 6-methyl-2-heptene, 2-ethyl-1-hexene, the $C_8$ olefin mixture obtained in the dimerization of butenes (dibutene), nonenes, 2- or 3-methyloctenes, the $C_9$ olefin mixture obtained in the trimerization of propene (tripropene), decenes, 2-ethyl-1-octene, dodecenes, the $C_{12}$ olefin mixture obtained in the tetramerization or the trimerization of butenes (tetrapropene or tributene), tetradecenes, hexadecenes, the $C_{16}$ olefin mixture obtained in the tetramerization of butenes (tetrabutane), and olefin mixtures prepared by cooligomerization of olefins having different numbers of carbon atoms (preferably 2 to 4).

The invention is illustrated in detail hereinafter by working examples and a FIGURE.

FIG. 1 shows a reaction apparatus in which the coupling reaction to give the corresponding unsymmetric biaryls can be conducted. The apparatus comprises a nickel cathode (1) and an anode composed of boron-doped diamond (BDD) on silicon (5). The apparatus can be cooled with the aid of a cooling jacket (3). The arrows indicate the flow direction of the cooling water. The reaction space is sealed by a Teflon stopper (2). The reaction mixture is mixed by a magnetic stirrer bar (7). On the anodic side, the apparatus is sealed by screw clamps (4) and seals (6).

ANALYSIS

Chromotography

The preparative liquid chromatography separations via flash chromatography were conducted with a maximum pressure of 1.6 bar on 60 M silica gel (0.040-0.063 mm) from Macherey-Nagel GmbH & Co, Düren. The unpressurized separations were conducted on Geduran Si 60 silica gel (0.063-0.200 mm) from Merck KGaA, Darmstadt. The solvents used as eluents (ethyl acetate (technical grade), cyclohexane (technical grade)) had been purified by distillation beforehand on a rotary evaporator.

For thin-layer chromatography (TLC), ready-made PSC silica gel 60 F254 plates from Merck KGaA, Darmstadt were used. The Rf values are reported as a function of the eluent mixture used. The TLC plates were stained using a cerium/molybdatophosphoric acid solution as immersion reagent. Cerium/molybdatophosphoric acid reagent 5.6 g of molybdatophosphoric acid, 2.2 g of cerium(IV) sulphate tetrahydrate and 13.3 g of concentrated sulphuric acid to 200 ml of water.

Gas Chromatography (GC/GCMS)

The gas chromatography studies (GC) on product mixtures and pure substances were effected with the aid of the GC-2010 gas chromatograph from Shimadzu, Japan. Analysis is effected on an HP-5 quartz capillary column from Agilent Technologies, USA (length: 30 m; internal diameter: 0.25 mm; film thickness of the covalently bound stationary phase: 0.25 µm; carrier gas: hydrogen; injector temperature: 250° C.; detector temperature: 310° C.; programme: "hard" method: start temperature 50° C. for 1 min, heating rate: 15° C./min, end temperature 290° C. for 8 min). Gas chromatography-mass spectrometry analyses (GC-MS) of product mixtures and pure substances were recorded with the aid of the GC-2010 gas chromatograph combined with the GCMS-QP2010 mass detector from Shimadzu, Japan. Analysis is effected on an HP-1 quartz capillary column from Agilent Technologies, USA (length: 30 m; internal diameter: 0.25 mm; film thickness of the covalently bound stationary phase: 0.25 µm; carrier gas: hydrogen; injector temperature: 250° C.; detector temperature: 310° C.; programme: "hard" method: start temperature 50° C. for 1 min, heating rate: 15° C./min, end temperature 290° C. for 8 min; GC-MS: ion source temperature: 200° C.).

Melting Points

Melting points were measured with the aid of the SG 2000 melting point determination instrument from HW5, Mainz, and are uncorrected.

Elemental Analysis

The elemental analyses were conducted in the analytical division of the Organic Chemistry department of the Johannes Gutenberg University of Mainz on a Varo EL Cube from Foss-Herseus, Hanau.

Mass Spectrometry

All electrospray ionization analyses (ESI+) were conducted on a QT of Ultima 3 from Waters Micromasses, Milford, Mass. EI mass spectra and the high-resolution EI spectra were analysed on an instrument of the MAT 95 XL sector field instrument type from ThermoFinnigan, Bremen.

NMR Spectroscopy

The NMR spectroscopy studies were conducted on multinucleus resonance spectrometers of the AC 300 or AV II 400 type from Bruker, Analytische Messtechnik, Karlsruhe. The solvent used was CDCl3. The 1H and 13C spectra were calibrated according to the residual content of undeuterated solvent using the NMR Solvent Data Chart from Cambridge Isotopes Laboratories, USA. Some of the 1H and 13C signals were assigned with the aid of H,H-COSY, H,H-NOESY, H,C-HSQC and H,C-HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported in hertz (Hz) together with the number of bonds covered. The numbering given in the assignment of signals corresponds to the numbering shown in the formula schemes, which do not necessarily have to correspond to IUPAC nomenclature.

General Procedures

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Synthesis of the Chlorophosphites

6-Chlorodibenzo[d,f][1,3,2]dioxaphosphepine was prepared according to DE 10 2008 043 584, and 2-chloro-4,4,5,5-tetraphenyl-1,3,2-dioxaphospholane according to DE 10 2006 058 682.

Synthesis of Unsymmetric Biaryls

The unsymmetric biaryls were prepared by an electrochemical method by coupling two phenols or one naphthol and one phenol which differ in terms of oxidation potential. In this regard, see also B. Elsier, D. Schollmeyer, K. M. Dyballa, R. Franke, S. R. Waldvogel, "Metall-und reagensfreie hochselektive anodische Kreuzkupplung von Phenolen" [Metal- and Reagent-Free High-Selectivity Anodic Cross-Coupling of Phenols], Angew. Chem., 2014, DOI: 10.1002/ange.201400627

General Procedure:

The coupling reaction was conducted in an apparatus as shown in FIG. 1.

5 mmol of the first phenol having an oxidation potential $E_{Ox}1$ together with 15 mmol of the second phenol having an oxidation potential $E_{Ox}2$ are dissolved in 1,1,1,3,3,3-hexafluoroisopropanol (HFIP) and MeOH or in formic acid and MeOH in the amounts specified in Table 1 below. The electrolysis is galvanostatic.

The outer shell of the electrolysis cell is kept at a controlled temperature of about 10° C. by means of a thermostat, while the reaction mixture is stirred and heated to 50° C. with the aid of a sand bath. After the electrolysis has ended, the cell contents are transferred together with toluene to a 50 ml round-bottom flask and the solvent is removed on a rotary evaporator at 50° C., 200-70 mbar, under reduced pressure. Unconverted reactant is recovered by means of short-path distillation (100° C., $10^{-3}$ mbar).

Electrode Material

Anode: boron-doped diamond (BDD) on Si
Cathode: Ni mesh

Electrolysis Conditions:

Temperature [T]: 50° C.
Current [I]: 15 mA
Current density [j]: 2.8 mA/cm$^2$
Charge [Q]: 2 F/mol of deficiency component
Terminal voltage [$U_{max}$]: 3:–5

The biaryls were synthesized by the general method described above, and in a reaction apparatus as shown in FIG. 1.

2,2'-Dihydroxy-4',5-dimethyl-5'-(methylethyl)-3-methoxybiphenyl

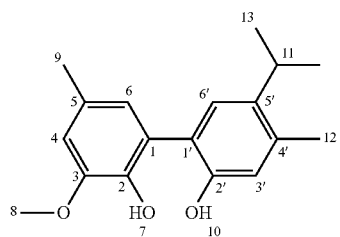

0.69 g (5 mmol, 1.0 equiv.) of 4-methylguaiacol and 2.28 g (15 mmol, 3.0 equiv.) of 3-methyl-4-(methylethyl)phenol were dissolved in 33 ml of HFIP, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 9:1 eluent (cyclohexane:ethyl acetate) and the product is obtained as a colourless solid.

Yield: 716 mg (50%; 2.5 mmol).
GC (hard method, HP-5): $t_R$=14.87 min
$R_f$(CH:EA=4:1)=0.43
$m_p$=126.8° C. (recrystallized from CH)
$^1$H-NMR (600 MHz, DMSO) δ=1.17-1.12 (m, 6H, 13-H), 2.24 (m, 6H, 9-H/12-H), 3.01 (dt, 1H, 11-H), 3.79 (s, 3H, 8-H), 6.55 (s, 1H, 6-H), 6.66 (d, 1H, 6'-H), 6.73 (d, 1H, 4-H), 6.96 (s, 1H, 3'-H), 8.16 (s, 1H, 7-H), 8.84 (s, 1H, 10-H);
Couplings: $^4J_{4-H,\ 6-H}$=2.2 Hz, $^4J_{6'-H,\ 11-H}$=2.9 Hz, $^3J_{11-H,\ 13-H}$=6.8 Hz;
$^{13}$C-NMR (151 MHz, DMSO) δ=18.73, 20.80 (C-9/C-12), 23.54 (C-13), 28.10 (C-11), 55.78 (C-8), 111.23 (C-4), 117.34 (C-6'), 123.42 (C-1'), 123.49 (C-6), 126.43 (C-1), 127.36 (C-5), 127.49 (C-3'), 134.40 (C-5'), 136.62 (C-4'), 141.12 (C-2), 147.65 (C-3), 151.69 (C-2').
HRMS for $C_{18}H_{22}O_3$ (ESI+) [M+Na$^+$]: calc: 309.1467, found: 309.1457
MS (EI, GCMS): m/z (%): 286 (50) [M]$^{+\bullet}$, 271 (100) [M-CH$_3^\bullet$]$^+$, 244 (22) [M-C$_3$H$_6^\bullet$]$^+$.
Elemental analysis for $C_{18}H_{22}O_3$: calc: C: 75.50%; H: 7.74%. found: C: 75.01%; H: 7.70%.

2,2'-Dihydroxy-5,5'-dimethyl-3-methoxybiphenyl

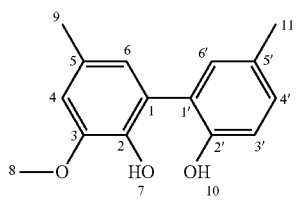

1.66 g (12 mmol, 1.0 equiv.) of 4-methylguaiacol and 3.91 g (36 mmol, 3.0 equiv.) of 4-methylphenol were dissolved in 65 ml of HFIP and 14 ml of MeOH, 1.63 g of methyltriethylammonium methylsulphate (MTES) were added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a colourless solid.

Yield: 440 mg (36%; 1.8 mmol).
GC (hard method, HP-5): $t_R$=13.56 min
$R_f$(CH:EA=4:1)=0.38
$m_p$=162.0° C. (recrystallized from CH)
$^1$H-NMR (400 MHz, DMSO) δ=2.18 (s, 3H, 9-H/11-H), 2.21 (s, 3H, 9-H/11-H), 3.76 (s, 3H, 8-H), 6.53 (s, 1H, 6-H), 6.71 (s, 1H, 4-H), 6.75 (d, 1H, 3'-H), 6.86-6.94 (m, 2H, 4'-H/6'-H), 8.53 (bs, 1H, 7-H/12-H);
Couplings: $^3J_{3'-H,\ 4'-H}$=8.4 Hz;
$^{13}$C-NMR (101 MHz, DMSO) δ =20.21, 20.77 (C-9/C-11), 55.79 (C-8), 111.36 (C-4), 115.69 (C-3'), 123.50 (C-6), 125.72 (C-1'), 126.16 (C-1), 127.20 (C-5), 127.30 (C-5'), 128.50 (C-6'), 131.83 (C-4'), 141.20 (C-2), 147.61 (C-3), 152.11 (C-2').
HRMS for $C_{15}H_{16}O_3$ (ESI+) [M+Na$^+$]: calc: 267.0997, found: 267.0999
MS (EI, GCMS): m/z (%): 244 (100) [M]$^{+\bullet}$, 229 (64) [M-CH$_3^\bullet$]$^+$.
Elemental analysis for $C_{15}H_{16}O_3$: calc: C: 73.75%; H: 6.60%. found: C: 73.81%; H: 6.54%.

2,2'-Dihydroxy-3-methoxy-3',5,5'-trimethylbiphenyl

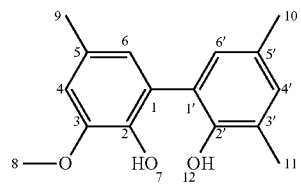

0.70 g (6 mmol, 1.0 equiv.) of 4-methylguaiacol and 2.08 g (17 mmol, 3.0 equiv.) of 2,4-dimethylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 9:1 eluent (cyclohexane:ethyl acetate) and the product is obtained as a pale yellow solid.

Yield: 663 mg (45%; 2.5 mmol).
GC (hard method, HP-5): $t_R$=13.97 min
$R_f$(CH:EA=4:1)=0.29
$m_p$=119.7° C. (recrystallized from DCM/CH)
$^1$H-NMR (400 MHz, CDCl$_3$) δ=2.34 (s, 3H, 10-H), 2.35 (s, 3H, 11-H), 2.38 (s, 3H, 9-H), 3.94 (s, 3H, 8-H), 6.16 (s, 1H, 12-H), 6.20 (s, 1H, 7-H), 6.76 (d, 1H, 4-H), 6.78 (d, 1H, 6-H), 6.98 (d, 1H, 6'-H), 7.03 (d, 1H, 4'-H);
Couplings: $^4J_{4-H,\ 6-H}$=1.7 Hz, $^4J_{4'-H,\ 6'-H}$=2.1 Hz;
$^{13}$C-NMR (101 MHz, CDCl$_3$) δ=16.51 (C-9), 20.54 (C-10), 21.20 (C-11), 56.12 (C-8), 110.92 (C-4), 123.95 (C-6), 124.13 (C-1), 124.64 (C-1'), 126.18 (C-3'), 128.82 (C-6'), 129.59 (C-5'), 130.40 (C-5), 131.40 (C-4'), 139.46 (C-2), 146.35 (C-3), 149.42 (C-2').

HRMS for $C_{18}H_{16}O_3$(ESI+) [M+Na$^+$]: calc: 281.1154, found: 281.1152

MS (EI, GCMS): m/z (%): 242 (100) [M]$^{+\bullet}$, 227 (38) [M-CH$_3^\bullet$]$^+$.

Elemental analysis for $C_{16}H_{18}O_3$: calc: C: 68.31%; H: 6.45%. found: C: 68.29%; H: 6.40%.

2,2'-Dihydroxy-3-methoxy-5-methyl-4'-(dimethylethyl)biphenyl

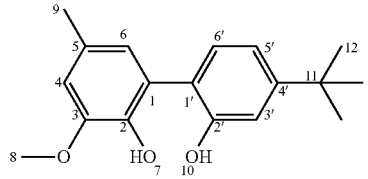

0.69 g (5 mmol, 1.0 equiv.) of 4-methylguaiacol and 2.25 g (15 mmol, 3.0 equiv.) of 3-tert-butylphenol were dissolved in 33 ml of HFIP, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a colourless solid.

Yield: 808 mg (63%; 3.1 mmol).
GC (hard method, HP-5): $t_R$=13.97 min
$R_f$(CH:EA=4:1)=0.29
$m_p$=160.3° C. (recrystallized from DCM/CH)
$^1$H-NMR (400 MHz, CDCl$_3$) δ=1.37 (s, 9H, 12-H), 2.36 (s, 3H, 9-H), 3.94 (s, 3H, 8-H), 6.25 (s, 1H, 7-H), 6.48 (s, 1H, 10-H), 6.75 (d, 1H, 6-H), 6.79 (d, 1H, 4-H), 7.08 (dd, 1H, 5'-H), 7.12 (d, 1H, 3'-H), 7.27 (d, 1H, 6'-H);
Couplings: $^4J_{4-H,\ 6-H}$=1.7 Hz; $^3J_{5'-H,\ 6'-H}$=8.0 Hz, $^4J_{3'-H,\ 5'-H}$=1.7 Hz;
$^{13}$C-NMR (101 MHz, CDCl$_3$) δ=21.24 (C-9), 31.31 (C-12), 34.58 (C-11), 56.15 (C-8), 110.79 (C-4), 114.94 (C-3'), 118.30 (C-5'), 122.37 (C-1'), 123.88 (C-1), 123.94 (C-6), 130.45 (C-6'), 130.53 (C-4'), 139.24 (C-5), 146.32 (C-3), 152.91 (C-2'), 153.13 (C-2).
HRMS for $C_{15}H_{16}O_4$ (ESI+) [M+Na$^+$]: calc: 309.1467, found: 309.1466
MS (EI, GCMS): m/z (%): 242 (100) [M]$^{+\bullet}$, 227 (38) [M-CH$_3^\bullet$]$^+$.
Elemental analysis for $C_{18}H_{22}O_3$: calc: 75.50%; H: 7.74%. found: C: 75.41%; H: 7.72%.

2,2'-Dihydroxyl-4',5-dimeth-3-methoxylbiphenyl 0.70 g (5 mmol, 1.0 equiv.) of 4-methylguaiacol and 1.65 g (15 mmol, 3.0 equiv.) of 3-methylphenol were dissolved in 33 ml of HFIP, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and two cross-coupling products are obtained as colourless solids.

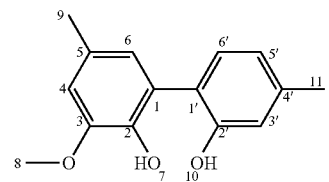

Yield: 266 mg (21%; 1.1 mmol).
GC (hard method, HP-5): $t_R$=13.72 min
$R_f$(CH:EA=4:1)=0.25
$m_p$=136.2° C. (recrystallized from DCM/CH)
$^1$H-NMR (400 MHz, CDCl$_3$) δ=2.35 (s, 3H, 9-H/11-H), 2.37 (s, 3H, 9-H/11-H), 3.94 (s, 3H, 8-H), 6.17 (s, 1H, 10-H), 6.35 (s, 1H, 2-H), 6.74 (d, 1H, 4-H), 6.76 (s, 1H, 6-H), 6.88-6.83 (m, 1H, 5'-H), 6.90 (d, 1H, 3'-H), 7.21 (d, 1H, 6'-H);
Couplings: $^4J_{4-H,\ 6-H}$=1.8 Hz, $^3J_{5'-H,\ 6'-H}$=7.7 Hz, $^4J_{3'-H,\ 5'-H}$=1.5 Hz;
$^{13}$C-NMR (101 MHz, CDCl$_3$) δ=21.11, 21.20 (C-9/C-11), 56.13 (C-8), 110.81 (C-4), 118.25 (C-3'), 121.97 (C-5'), 122.39 (C-1), 123.77 (C-1'), 123.85 (C-6), 130.50 (C-5), 130.68 (C-6'), 139.30 (C-4'), 139.54 (C-2), 146.31 (C-3), 153.33 (C-2').
HRMS for $C_{15}H_{16}O_3$ (ESI+) [M+•Na$^+$]: calc: 267.0997, found: 267.1006
MS (EI, GCMS): m/z (%): 244 (100) [M]$^{+\bullet}$, 229 (18) [M-CH$_3^\bullet$]$^+$.
Elemental analysis for $C_{15}H_{16}O_3$: calc: C: 73.75%; H: 6.60%. found: C: 73.70%; H: 6.68%.

2,2'-Dihydroxy-3-methoxy-4',5, 5'-trimethylbiphenyl

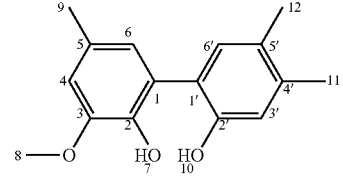

0.69 g (5 mmol, 1.0 equiv.) of 4-methylguaiacol and 1.83 g (15 mmol, 3.0 equiv.) of 3,4-dimethylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 9:1 eluent (cyclohexane:ethyl acetate) and the product is obtained as a colourless solid.

Yield: 688 mg (52%; 2.6 mmol).
GC (hard method, HP-5): $t_R$=14.52 min
$R_f$(CH:EA=4:1)=0.29
$m_p$=152.3° C. (recrystallized from DCM/CH)
$^1$H-NMR (400 MHz, CDCl$_3$) δ=12.25 (s, 3H, 11-H), 2.28 (s, 3H, 12-H), 2.36 (s, 3H, 9-H), 3.93 (s, 3H, 8-H), 6.19 (s, 1H, 7-H), 6.25 (s, 1H, 10-H), 6.73 (d, 1H, 4-H), 6.76 (s, 1H, 6-H), 6.88 (s, 1H, 3'-H), 7.08 (s, 1H, 6'-H);
Couplings: $^4J_{4-H,\ 6-H}$=1.7 Hz;
$^{13}$C-NMR (101 MHz, CDCl$_3$) δ=18.89 (C-11), 19.60 (C-12), 21.24 (C-9), 56.14 (C-8), 110.74 (C-4), 118.93

(C-3'), 122.54 (C-1), 123.82 (C-6), 123.97 (C-1'), 129.03 (C-5), 130.46 (C-4'), 131.69 (C-6'), 137.94 (C-5'), 139.26 (C-2), 146.31 (C-3), 151.36 (C-2').

HRMS for $C_{16}H_{18}O_3$(ESI+) [M+Na$^{30}$]: calc: 281.1154, found: 281.1157

MS (EI, GCMS): m/z (%): 258 (100) [M]$^{+•}$, 243 (10) [M-CH$_3$$^•$]$^+$.

Elemental analysis for $C_{16}H_{18}O_3$: calc: 74.39%; H: 7.02%. found: C: 74.32%; H: 7.20%.

2,2'-Dihydroxy-5'-isopropyl-3-methoxy-5-methylbiphenyl

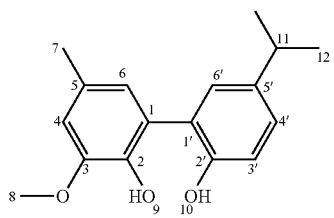 [SMILES: COc1cc(C)cc(-c2cc(C(C)C)ccc2O)c1O]

0.69 g (5 mmol, 1.0 equiv.) of 4-methylguaiacol and 2.05 g (15 mmol, 3.0 equiv.) of 4-isopropylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a brownish oil.

Yield: 0.53 g (39%, 1.9 mmol)
GC (hard method, HP-5): $t_R$=14.23 min
$R_f$(CH:EA=4:1)=0.30
$^1$H-NMR (400 MHz, CDCl$_3$) δ=1.27 (m, 6H), 2.36 (s, 3H), 2.91 (dt, J=13.8, 6.9, 6.9 Hz, 1H), 3.94 (s, 3H), 6.13-6.27 (m, 2H), 6.82-6.65 (m, 1H), 6.25 (m, 2H), 6.75 (s, 1H), 6.77 (s, 1H), 6.99 (d, J=8.1 Hz, 1H), 7.19-7.12 (m, 2H);
$^{13}$C-NMR (101 MHz, CDCl$_3$) δ=21.25, 24.27, 33.40, 56.18, 110.92, 117.60, 123.91, 124.23, 125.07, 127.29, 128.80, 130.57, 139.29, 141.42, 146.31, 151.51.
HRMS for $C_{17}H_{20}O_3$ (ESI+) [M+Na$^{30}$]: calc: 295.1310, found: 295.1297
MS (EI, GCMS): m/z (%): 272 (80) [M]$^{+•}$, 257 (100) [M-CH$_3$$^•$]$^+$.

2,2'-Dihydroxy-3-methoxy-5-methyl-5'-tert-butylbiphenyl

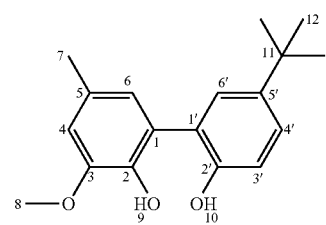

0.69 g (5 mmol, 1.0 equiv.) of 4-methylguaiacol and 2.26 g (15 mmol, 3.0 equiv.) of 4-tert-butylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a yellowish oil.

Yield: 0.48 g (34%, 1.7 mmol)
GC (hard method, HP-5): $t_R$=14.52 min
$R_f$(CH:EA=4:1)=0.24
$^1$H-NMR (400 MHz, CDCl$_3$) δ=1.34 (s, 9H), 2.37 (s, 3H), 3.94 (s, 3H), 6.17 (s, 1H), 6.24 (s, 1H), 6.75 (s, 1H), 6.77 (s, 1H), 6.99 (d, J=8.4 Hz, 1H), 7.31-7.29 (m, 1H), 7.33 (dd, J=8.4, 2.5 Hz, 1H).
$^{13}$C-NMR (101 MHz, CDCl$_3$) δ=21.28, 31.61, 34.20, 56.18, 110.91, 117.25, 123.92, 124.41, 124.63, 126.38, 127.78, 130.58, 139.32, 143.70, 146.32, 151.22.
HRMS for $C_{18}H_{22}O_3$ (ESI+) [M+Na$^{30}$]: calc: 309.1467, found: 309.1476
MS (EI, GCMS): m/z (%): 286 (28) [M]$^{+•}$, 271 (100) [M-CH$_3$$^•$]$^+$.

2,2'-Dihydroxy-3',5'-di-tert-butyl-5-methyl-3-methoxybiphenyl

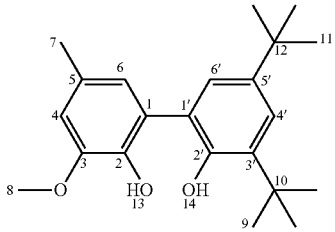 [SMILES: COc1cc(C)cc(-c2cc(C(C)(C)C)cc(C(C)(C)C)c2O)c1O]

0.69 g (5 mmol, 1.0 equiv.) of 4-methylguaiacol and 3.12 g (15 mmol, 3.0 equiv.) of 2,4-di-tert-butylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 9:1 eluent (cyclohexane:ethyl acetate) and the product is obtained as a colourless solid.

Yield: 0.41 g (24%, 1.2 mmol)
GC (hard method, HP-5): $t_R$=15.15 min
$R_f$(CH:EA=9:1)=0.35
$m_p$=120.2° C. (recrystallized in n-pentane)
$^1$H-NMR (400 MHz, CDCl$_3$) δ=1.36 (s, 9H), 1.50 (s, 9H), 2.38 (s, 3H), 3.96 (s, 3H), 6.00 (s, 1H), 6.05 (s, 1H), 6.77 (s, 1H), 7.16 (d, J=2.5 Hz, 1H), 7.39 (d, J=2.5 Hz, 1H).
$^{13}$C-NMR (101 MHz, CDCl$_3$) δ=21.23, 29.88, 31.69, 34.40, 35.23, 56.17, 111.03, 123.96, 124.17, 125.09, 125.50, 130.42, 136.73, 139.72, 142.36, 146.45, 149.82.
MS (EI, GCMS): m/z (%): 342 (22) [M]$^{+•}$, 327 (100) [M-CH$_3$$^•$]$^+$.

2,2'-Dihydroxy-3',5-dimethyl-3-methoxy-5'-tert-butylbiphenyl

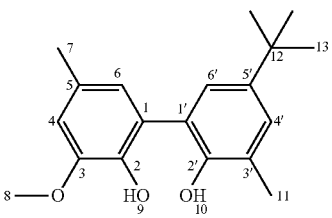 [SMILES: COc1cc(C)cc(-c2cc(C(C)(C)C)cc(C)c2O)c1O]

0.69 g (5 mmol, 1.0 equiv.) of 4-methylguaiacol and 2.47 g (15 mmol, 3.0 equiv.) of 2-methyl-4-tert-butylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a yellowish oil.

Yield: 0.69 g (46%, 2.3 mmol)

GC (hard method, HP-5): $t_R$=14.79 min $R_f$(CH:EA=4:1)=0.33

$^1$H-NMR (400 MHz, CDCl$_3$) δ=1.37 (s, 9H), 2.39 (d, J=2.4 Hz, 6H), 3.94 (s, 3H), 6.15 (s, 1H), 6.17 (s, 1H), 6.77 (s, 1H), 6.79 (s, 1H), 7.17 (d, J=2.5 Hz, 1H), 7.24 (d, J=2.4 Hz, 1H);

$^{13}$C-NMR (101 MHz, CDCl$_3$) δ=16.90, 21.28, 31.67, 34.12, 56.16, 110.94, 124.02, 124.17, 124.59, 125.41, 125.65, 127.86, 130.47, 139.50, 143.07, 146.40, 149.41.

MS (EI, GCMS): m/z (%): 300 (18) [M]$^{+\bullet}$, 285 (100) [M-CH$_3^\bullet$]$^+$.

2,2'-Dihydroxy-3-methoxy-5-methyl-5'-(1-methylethyl)biphenyl

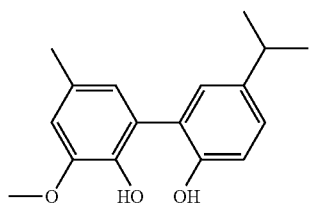 [SMILES: COc1cc(C)cc(-c2cc(C(C)C)ccc2O)c1O]

0.69 g (5 mmol, 1.0 eq.) of 4-methylguaiacol and 2.05 g (15 mmol, 3.0 eq.) of 4-isopropylphenol and 0.68 g of methyltriethylammonium methylsulphate (MTES) in 27 ml of HFIP+6 ml of MeOH were added to methyltriethylammonium methylsulphate (MTES) and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a brownish oil.

Yield: 39% 527 mg, 1.9 mmol.

$R_f$(cyclohexane:ethyl acetate=4:1)=0.30; $^1$H NMR (400 MHz, CDCl$_3$) δ=1.27 (m, 6H), 2.36 (s, 3H), 2.91 (sept, J=6.9 Hz, 1H), 3.94 (s, 3H), 6.13-6.27 (m, 2H), 6.65-6.82 (m, 2H), 6.99 (d, J=8.1 Hz, 1H), 7.12-7.19 (m, 2H); $^{13}$C NMR (101 MHz, CDCl$_3$) δ=21.37, 24.39, 33.53, 56.31, 111.04, 117.73, 124.04, 124.36, 125.20, 127.42, 128.93, 130.70, 139.42, 141.55, 146.44, 151.64. HRMS for C$_{17}$H$_{20}$O$_3$(ESI+) [M+Na$^{30}$]: calc.: 295.1310, found: 295.1297. MS (EI, GCMS): m/z (%): 272 (80) [M]$^{+\bullet}$, 257 (100) [M-CH$_3^\bullet$]$^+$.

2,2'-Dihydroxy-3-methoxy-5-methyl-4'-(methylethyl)biphenyl

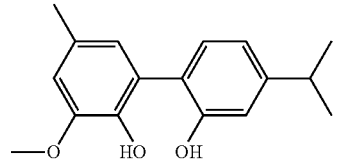 [SMILES: COc1cc(C)cc(-c2ccc(C(C)C)cc2O)c1O]

0.69 g (5 mmol, 1.0 eq.) of 4-methylguaiacol and 2.065 g (15 mmol, 3.0 eq.) of 3-isopropylphenol and 0.68 g of methyltriethylammonium methylsulphate (MTES) were dissolved in 33 ml of HFIP and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a brownish oil (yield: 52%, 705 mg, 2.6 mmol).

$R_f$ (cyclohexane:ethyl acetate=4:1)=0.29; $^1$H NMR (400 MHz, CDCl$_3$) δ=1H NMR (400 MHz, CDCl3) δ 1.27 (s, 3H), 1.29 (s, 3H), 2.34 (s, 3H), 2.91 (sept, J=7.0 Hz, 1H), 3.94 (s, 3H), 6.15 (s, 1H), 6.35 (s, 1H), 6.73 (d, J=1.8 Hz, 1H), 6.75-6.77 (m, 1H), 6.90 (dd, J=7.9 Hz, 1.8 Hz, 1H), 6.94 (d, J=1.7 Hz, 1H), 7.23 (d, J=7.8 Hz, 1H). $^{13}$C NMR (101 MHz, CDCl$_3$) δ=$^{13}$C NMR (101 MHz, CDCl$_3$) δ 21.36, 24.02, 33.92, 56.30, 77.16, 110.91, 115.77, 119.56, 122.81, 124.00, 124.08, 130.65, 130.84, 139.38, 146.43, 150.72, 153.54. HRMS for C$_{17}$H$_{20}$O$_3$ (ESI+) [M+Na$^{30}$]: calc.: 295.1310. found: 295.1305; MS (EI, GCMS): m/z (%): 272 (100) [M]$^{+\bullet}$, 257 (50) [M-CH$_3^\bullet$]$^+$.

Elemental analysis for C$_{17}$H$_{20}$O$_3$: calc.: 74.97%; H: 7.40%. found: C: 75.05%; H: 7.36%.

2,2'-Dihydroxy-4',5-dimethyl-3-methoxybiphenyl 0.28 g (2 mmol, 1.0 eq.) of 4-methylguaiacol, 1.22 g (6 mmol, 3.0 eq.) of 3-methylphenol and 0.77 g of MTBS were dissolved in 25 ml of HFIP and the electrolyte was transferred to the beaker-type electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and this led to the two cross-coupling products as a colourless and viscous oil.

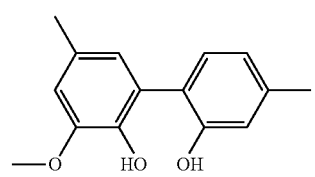

Yield: 21%, 266 mg, 1.1 mmol; $R_f$ (cyclohexane:ethyl acetate=4:1)=0.25; $m_p$=136.2° C. (crystallized from dichloromethane/cyclohexane); $^1$H NMR (400 MHz, CDCl$_3$) δ=2.35 (s, 3H), 2.37 (s, 3H,), 3.94 (s, 3H), 6.17 (s, 1H), 6.35 (s, 1H), 6.74 (d, J=1.8 Hz, 1H), 6.76 (s, 1H), 6.88-6.83 (m, 1H), 6.90 (d, 1H, J=1.5 Hz), 7.21 (d, 1H, J=7.7 Hz); $^{13}$C NMR (101 MHz, CDCl$_3$) δ=21.11, 21.20 56.13, 110.81, 118.25, 121.97, 122.39, 123.77, 123.85, 130.50, 130.68, 139.30, 139.54, 146.31, 153.33. HRMS for C$_{15}$H$_{16}$O$_3$ (ESI+) [M+Na$^+$]: calc.: 267.0997, found: 267.1006; MS (EI, GCMS): m/z (%): 244 (100) [M]$^{+\bullet}$, 229 (18) [M-CH$_3^\bullet$]$^{+\bullet}$. Elemental analysis for C$_{15}$H$_{16}$O$_3$: calc. C: 73.75%; H: 6.60%. found: C: 73.70%; H: 6.68%.

2,2'-Dihydroxy-5,5'-dimethyl-3'-(1,1-dimethylethyl)-3-methoxybiphenyl

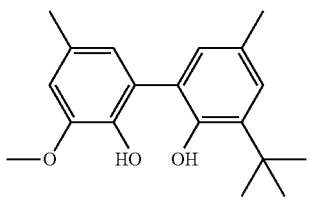 [SMILES: COc1cc(C)cc(-c2cc(C)cc(C(C)(C)C)c2O)c1O]

0.69 g (5 mmol, 1.0 eq.) of 4-methylguaiacol, 2.47 g (15 mmol, 3.0 eq.) of 4-methyl-2-tert-butylphenol and 0.68 g of methyltriethylammonium methylsulphate (MTES) were dissolved in 27 ml of HFIP+6 ml of MeOH and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a yellow oil (yield: 36%, 545 mg, 1.8 mmol).

R$_f$ (cyclohexane:ethyl acetate=9:1)=0.36; $^1$H NMR (400 MHz, CDCl$_3$) δ=1.46 (s, 9H), 2.34 (m, 6H), 3.93 (s, 3H), 5.99 (s, 1H), 6.01 (s, 1H), 6.74 (s, 2H), 6.96 (d, J=1.9 Hz, 1H), 7.14 (d, J=1.9 Hz, 1H); $^{13}$C NMR (101 MHz, CDCl$_3$) δ=21.05, 21.32, 29.96, 35.05, 56.30, 77.16, 111.21, 124.18, 124.24, 125.92, 127.67, 129.15, 129.22, 130.51, 137.57, 139.87, 146.57, 150.10. HRMS for C$_{22}$H$_{30}$O$_3$(ESI+) [M+Na$^+$]: calc.: 323.1623, found: 323.1618; MS (EI, GCMS): m/z (%): 300 (100) [M]$^{+\bullet}$, 285 (100) [M-CH$_3^\bullet$]$^+$.

1-(2-Hydroxy-3-methoxy-5-methylphenyl)-2-naphthol

The electrolysis was conducted according to the general procedure in an undivided flange cell with a BDD anode. For this purpose, 0.78 g (5 mmol, 1.0 equiv.) of 2-naphthol and 2.18 g (15 mmol, 3.0 equiv.) of 4-methylguaiacol are dissolved in 27 ml of HFIP and 6 ml of MeOH, 0.68 g of methyltriethylammonium methylsulphate (MTES) is added and the electrolyte is transferred to the electrolysis cell. The solvent and unconverted amounts of reactant are removed under reduced pressure after the electrolysis, the crude product is purified by flash chromatography on silica gel 60 in a 4:1 eluent (CH:EA) and a product mixture is obtained. A second flash chromatography in dichloromethane enables a separation of the two components as a pale red crystalline main product and a colourless crystalline by-product.

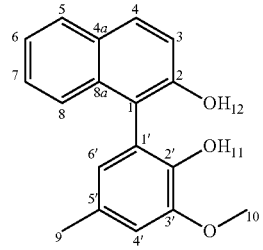 [SMILES: COc1cc(C)cc(-c2c(O)ccc3ccccc23)c1O]

Yield: 899 mg (61%; 3.2 mmol).
GC (hard method, HP-5): t$_R$=15.77 min
R$_f$(CH:EA=4:1)=0.36, R$_1$(DCM)=0.36
m$_p$=145.5° C. (recrystallized from DCM/CH)
$^1$H-NMR (400 MHz, CDCl$_3$) δ=2.39 (s, 3H, 9-H), 3.96 (s, 3H, 10-H), 5.47-5.52 (m, 1H, 12-H), 5.65-5.69 (m, 1H, 11-H), 6.75 (d, 1H, 6'-H), 6.85 (d, 1H, 4'-H), 7.32 (dd, 1H, 3-H), 7.34-7.43 (m, 2H, 6-H/7-H), 7.51 (d, 1H, 8-H), 7.83 (s, 1H, 5-H), 7.85 (d, 1H, 4-H);
Couplings: $^3J_{3\text{-}H,\ 4\text{-}H}$=9.0 Hz, $^3J_{7\text{-}H,\ 8\text{-}H}$=8.3 Hz, $^4J_{4'\text{-}H,\ 6'\text{-}H}$=1.8 Hz;
$^{13}$C-NMR (101 MHz, CDCl$_3$) δ=21.22 (C-9), 56.08 (C-10), 112.06 (C-4'), 116.62 (C-1), 117.81 (C-3), 119.33 (C-1'), 123.36 (C-6/C-7), 124.42 (C-6'), 124.86 (C-8), 126.48 (C-6/C-7), 128.15 (C-4), 129.18 (C-4a), 129.83 (C-5), 130.36 (C-5'), 133.16 (C-8a), 141.72 (C-2'), 147.24 (C-3'), 150.84 (C-2).
HRMS for C$_{18}$H$_{16}$O$_3$(ESI+) [M+Na$^+$]: calc: 303.0997, found: 303.1003
MS (EI, GCMS): m/z (%): 280 (100) [M]$^{+\bullet}$, 265 (12) [M-CH$_3^\bullet$]$^{+\bullet}$, 249 (12) [M-OCH$_3^\bullet$]$^+$.
Elemental analysis for C$_{18}$H$_{16}$O$_3$: calc: C: 77.12%; H: 5.75%. found: C: 76.96%; H: 5.82%.

1-(3-(Dimethylethyl)-2-hydroxy-5-methoxyphenyl-2-naphthol

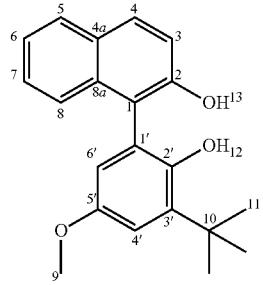 [SMILES: COc1cc(-c2c(O)ccc3ccccc23)c(O)c(C(C)(C)C)c1]

The electrolysis was conducted according to general procedure 1 in an undivided flange cell with a BDD anode. For this purpose, 0.72 g (5 mmol, 1.0 equiv.) of 2-naphthol and 2.77 g (15 mmol, 3.0 equiv.) of 2-(dimethylethyl)-4-methoxyphenol are dissolved in 27 ml of HFIP and 6 ml of MeOH, 0.68 g of methyltriethylammonium methylsulphate (MTES) is added and the electrolyte is transferred to the electrolysis cell. The solvent and unconverted amounts of reactant are removed under reduced pressure after the electrolysis, the crude product is purified by flash chromatography on silica gel 60 in a 9:1 eluent (CH:EA) and the product is obtained as a colourless solid.
Yield: 1.05 g (63%, 3.2 mmol)

GC (hard method, HP-5): $t_R$=15.75 min
$R_f$(CH:EA=4:1)=0.43
$m_p$=139.9° C. (recrystallized from DCM/CH)
$^1$H-NMR (400 MHz, CDCl$_3$) δ=1.46 (s, 9H, 11-H), 3.77 (s, 3H, 9-H), 4.72 (s, 1H, 2'-H), 5.36 (s, 1H, 2-H), 6.63 (d, 1H, 6'-H), 7.08 (d, 1H, 4'-H), 7.32 (d 1H, 3-H), 7.50-7.35 (m, 3H, 6-H/7-H/8-H), 7.87-7.83 (m, 1H, 5-H), 7.89 (d, 1H, 4-H);
Couplings: $^3J_{3\text{-}H,\ 4\text{-}H}$=8.9 Hz; $^4J_{4'\text{-}H,\ 6'\text{-}H}$=3.1 Hz;
$^{13}$C-NMR (101 MHz, CDCl$_3$) δ=29.41 (C-11), 35.19 (C-10), 55.68 (C-9), 111.95 (C-6'), 114.18 (C-1), 115.87 (C-4'), 117.63 (C-3), 119.16 (C-1'), 123.89, 124.15 (C-6/C-8), 127.38 (C-7), 128.31 (C-5), 129.19 (C-4a), 130.97 (C-4), 132.99 (C-8a), 139.05 (C-3'), 146.93 (C-2'), 151.94 (C-2), 153.41 (C-5').
HRMS for C$_{21}$H$_{22}$O$_3$(ESI+) [M+Na$^+$]: calc: 345.1467, found: 345.1465
MS (EI, GCMS): m/z (%): 322 (100) [M]$^{+\bullet}$, 307 (38) [M-CH$_3^\bullet$]$^+$.
Elemental analysis for C$_{21}$H$_{22}$O$_3$: calc: 78.23%; H: 6.88%. found: C: 78.18%; H: 6.82%.

Synthesis of the Ligands 6-((1-(2-(Dibenzo[d,f][1,3,2]dioxaphosphepin-6-yloxy)-3-methoxy-5-methylphenyl)naphthalen-2-yl)oxy)dibenzo[d,f][1,3,2]dioxaphosphepine

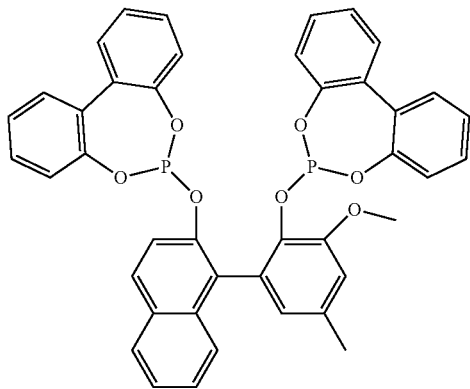

(1)

To a stirred suspension of 1-(2-hydroxy-3-methoxy-5-methylphenyl)naphthalen-2-ol (0.309 g; 1.103 mmol) in toluene (6 ml) was added triethylamine (0.467 g; 4.610 mmol), and the mixture was cooled to 0° C. To this mixture was added dropwise a solution of 6-chlorodibenzo[d,f][1,3,2]dioxaphosphepine (0.676 g; 2.696 mmol) in toluene (9 ml). The reaction mixture was stirred overnight and then filtered. The resulting solid was taken up in 50 ml of toluene. The suspension was stirred at 40° C. for 2 h and then filtered while warm. The filtrate was concentrated to dryness. Yield: 0.403 g (0.569 mmol; 52%).
Elemental analysis (calc. for C$_{42}$H$_{30}$O$_7$P$_2$=708.60 g/mol) C 71.37 (71.19); H 4.34 (4.27); P 8.87 (8.74) %.
$^{31}$P-NMR (CD$_2$Cl$_2$): 145,7 (d, J$_{PP}$=17.5 Hz); 147,6 (d, J$_{PP}$=17,5 Hz) ppm.
$^1$H-NMR (CD$_2$Cl$_2$): 2,48 (m, 3 H); 4,09 (s, 3 H); 6,36 (m, 1 H, H$_{arom}$); 6,41-6,49 (m, 1 H, H$_{arom}$); 6,83 (m, 1 H, H$_{arom}$); 6,89-6,97 (m, 1 H, H$_{arom}$); 7,00-7,10 (m, 3 H, H$_{arom}$); 7,10-7,18 (m, 1 H, H$_{arom}$); 7,18-7,26 (m, 2 H, H$_{arom}$); 7,26-7,41 (m, 6 H, H$_{arom}$); 7,42-7,60 (m, 6 H, H$_{arom}$); 7,98-8,09 (m, 2 H, H$_{arom}$) ppm.
$^{13}$C-NMR (CD$_2$Cl$_2$): 21,5; 57,0; 114,1; 121,3 (d, J$_{CP}$=9,0 Hz); 122,3 (d, J$_{CP}$=5,3 Hz); 122,5 (d, J$_{CP}$=4,0 Hz); 125,2; 125,3; 125,5; 125,7; 125,8; 126,4; 127,3; 128,3; 128,7 (d, J$_{CP}$=3,0 Hz); 129,0; 129,2; 129,4; 129,6; 129,7 (d, J$_{CP}$=5,2 Hz); 130,0; 130,1 (d, J$_{CP}$=4,9 Hz); 131,3; 131,5; 134,1; 134,8; 138,6; 147,6 (d, J$_{CP}$=8,1 Hz); 149,4 (m); 151,5 (d, J$_{CP}$=2,5 Hz) ppm.

2-(2-Methoxy-4-methyl-6-(2-(4,4,5,5-tetraphenyl-1,3,2-dioxaphospholan-2-yl)oxy)naphthalen-1-yl)phenoxy)-4,4,5,5-tetraphenyl-1,3,2-dioxaphospholane

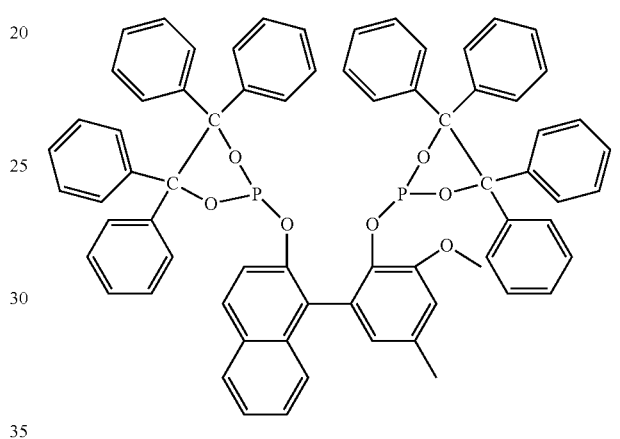

(2)

To a stirred suspension of 1-(2-hydroxy-3-methoxy-5-methylphenyl)naphthalen-2-ol (0.396 g; 1.413 mmol) in toluene (8 ml) was added triethylamine (0.448 g; 4.429 mmol), and the mixture was cooled to 0° C. Added dropwise to this mixture was a solution of 2-chloro-4,4,5,5-tetraphenyl-1,3,2-dioxaphospholane (1.332 g; 3.092 mmol) in toluene (12 ml), and the resulting mixture was stirred at 0° C. for 45 min. Then the reaction mixture was stirred at room temperature overnight and at 70° C. for 2 h. Thereafter, the mixture was filtered and the solvent was removed under reduced pressure. The resulting pale yellow solid was dried at 50° C. for 4 h and recrystallized from THF/diethyl ether (7 ml/34 ml). Yield: 1.334 g (1.248 mmol; 87%).
Elemental analysis (calc. for C$_{70}$H$_{54}$O$_7$P$_2$=1069.12 g/mol) C 78.62 (78.63); H 5.30 (5.09); P 5.86 (5.79) %.
$^{31}$P-NMR (THF-d$_8$): 140,9 (d, J$_{PP}$=20,7 Hz); 144,4 (d, J$_{PP}$=20,7 Hz) ppm.
$^1$H-NMR (THF-d$_8$): 2,39 (m, 3 H); 3,86 (s, 3 H); 6,62-6,75 (m, 5 H, H$_{arom}$); 6,76-6,82 (m, 1 H, H$_{arom}$); 6,86-6,98 (m, 7 H, H$_{arom}$); 6,98-7,07 (m, 19 H, H$_{arom}$); 7,07-7,15 (m, 8 H, H$_{arom}$); 7,34-7,40 (m, 2 H, H$_{arom}$); 7,40-7,49 (m, 4 H, H$_{arom}$); 7,76 (m, 1 H, H$_{arom}$); 7,86 (m, 1 H, H$_{arom}$) ppm.
$^{13}$C-NMR (CD$_2$Cl$_2$): 21,5; 57,2; 94,7 (d, J$_{CP}$=8,8 Hz); 95,3 (d, J$_{CP}$=8,6 Hz); 95,4 (d, J$_{CP}$=8,3 Hz); 114,5; 121,9 (d, J$_{CP}$=8,2 Hz); 124,9; 126,0; 126,6; 126,7; 126,8; 127,0; 127,1; 127,2; 127,3; 127,3; 127,4; 127,5; 128,1; 129,0; 129,1; 129,4; 129,4; 130,0; 130,1; 130,2; 131,0; 133,9; 134,1; 139,3 (d, J$_{CP}$=6,9 Hz); 142,4 (d, J$_{CP}$=3,9 Hz); 142,6 (d, J$_{CP}$=3,9 Hz); 142,8 (d, J$_{CP}$=8,8 Hz); 143,0 (d, J$_{CP}$=4,5 Hz); 147,2 (d, J$_{CP}$=7,5 Hz); 151,3 (d, J$_{CP}$=3,3 Hz) ppm.

6,6'-((4'-(tert-Butyl)-3-methoxy-5-methyl-[1,1'-biphenyl]-2,2'-diyl)bis(oxy))didibenzo[d,f][1,3,2]dioxaphosphepine (3)

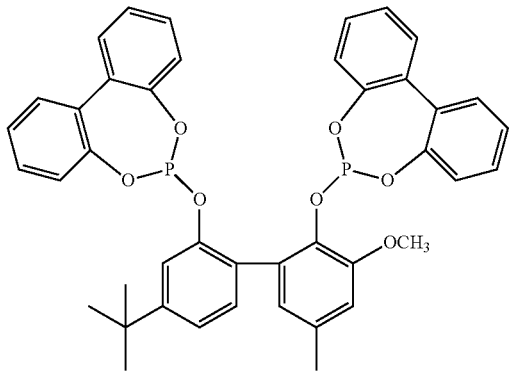

To a solution of 4'-(tert-butyl)-3-methoxy-5-methyl-[1,1'-biphenyl]-2,2'-diol (0.489 g; 1.708 mmol) in toluene (12 ml) was added pyridine (0.389 g; 3.844 mmol), and the resulting mixture was added dropwise at 3° C. to a solution of 6-chlorodibenzo[d,f][1,3,2]dioxaphosphepine (0.942 g; 3.758 mmol) in toluene (12 ml). The reaction mixture was stirred overnight and then filtered. The filtrate was concentrated to dryness under vacuum and the resulting residue was dried at 50° C./0.1 mbar. The remaining substance was purified by column chromatography (hexane/toluene, 1:2, $R_f$=0.3). Yield: 0.738 g (1.032 mmol; 58%).

Elemental analysis (calc. for $C_{42}H_{36}O_7P_2$=714.69 g/mol) C 70.59 (70.58); H 5.28 (5.08); P 8.85 (8.67) %.

$^{31}$P-NMR (CD$_2$Cl$_2$): 144,3 (d, $J_{PP}$=9,1 Hz); 148,1 (d, $J_{PP}$=9,1 Hz) ppm.

$^1$H-NMR (CD$_2$Cl$_2$): 1,51 (m, 9 H); 2,45 (m, 3 H); 4,06 (s, 3 H); 6,80-6,87 (m, 3 H, H$_{arom}$); 6,98-7,03 (m, 2 H, H$_{arom}$); 7,03-7,05 (m, 1 H, H$_{arom}$); 7,28-7,35 (m, 8 H, H$_{arom}$); 7,35-7,38 (m, 1 H, H$_{arom}$); 7,38-7,43 (m, 2 H, H$_{arom}$); 7,46-7,54 (m, 4 H, H$_{arom}$) ppm.

$^{13}$C-NMR (CD$_2$Cl$_2$): 21,5; 57,0; 113,8; 118,4 (d, $J_{CP}$=10,1 Hz); 121,8; 122,5 (d, $J_{CP}$=14,1 Hz); 124,9; 125,5 (d, $J_{CP}$=17,3 Hz); 127,9; 128,7; 129,4; 129,4 (d, $J_{CP}$=16,8 Hz); 130,1 (d, $J_{CP}$=16.1 Hz); 131,3; 131,5; 131,6; 132,0; 134,4; 138,0; 149,5 (d, $J_{CP}$=4,8 Hz); 149,7 (d, $J_{CP}$=4,4 Hz); 149,8 (d, $J_{CP}$=7.0 Hz); 151,2 (d, $J_{CP}$=3.2 Hz); 153,4 ppm.

2,2'-((5'-(tert-Butyl)-3-methoxy-5-methyl-[1,1'-biphenyl]-2,2'-diyl)bis(oxy))bis(4,4,5,5-tetraphenyl-1,3,2-dioxaphospholan (4)

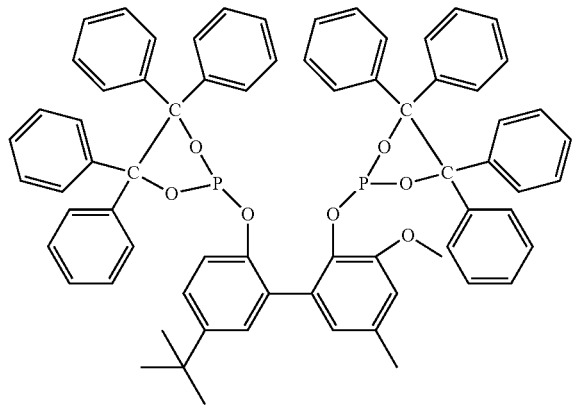

To a solution of 4'-(tert-butyl)-3-methoxy-5-methyl-[1,1'-biphenyl]-2,2'-diol (0.327 g; 1.143 mmol) in THF (5 ml) were added 2 equivalents of n-butyllithium in hexane (4.3 ml) at −20° C. The mixture was stirred at −20° C. for 20 min and, after warming to room temperature, a solution of 2-chloro-4,4,5,5-tetraphenyl-1,3,2-dioxaphospholane (0.985 g; 2.287 mmol) in THF (8 ml) was added. The reaction mixture was stirred overnight and the solvent was drawn off under reduced pressure. Toluene (20 ml) was added and the resulting solution was filtered. The cloudy filtrate was filtered once again through silica gel and the solvent was removed under reduced pressure. The resulting solid was dried at 50° C./0.1 mbar and then recrystallized from hot acetonitrile (11 ml). Yield: 0.840 g (0.781 mmol; 68%).

Elemental analysis (calc. for $C_{70}H_{60}O_7P_2$=1075.19 g/mol) C 78.36 (78.20); H 5.75 (5.62); P 5.95 (5.76) %.

$^{31}$P-NMR (CD$_2$Cl$_2$): 139,3 (d, $J_{PP}$=13,6 Hz); 145.2 (d, $J_{PP}$=13,6 Hz) ppm.

$^1$H-NMR (CD$_2$Cl$_2$): 1,26 (m, 9 H); 2,38 (m, 3 H); 3,95 (s, 3 H); 6,54 (m, 1 H, H$_{arom}$); 6,70 (m, 1 H, H$_{arom}$); 6,91 (m, 1 H, H$_{arom}$); 6,98-7,04 (m, 4 H, H$_{arom}$); 7,05-7,13 (m, 20 H, H$_{arom}$); 7,13-7,21 (m, 10 H, H$_{arom}$); 7,33-7,40 (m, 4 H, H$_{arom}$); 7,49-7,55 (m, 4 H, H$_{arom}$) ppm.

$^{13}$C-NMR (CD$_2$Cl$_2$): 31,5; 57,4; 94,9 (d, $J_{CP}$=9,0 Hz); 95,3 (d, $J_{CP}$=8,5 Hz); 114,2; 118,9 (d, $J_{CP}$=9,0 Hz); 121,1; 125,6; 127,2; 127,3; 127,4; 127,5; 127,6; 127,9; 127,9; 129,1 (d, $J_{CP}$=3,0 Hz); 129,2 (d, $J_{CP}$=3,0 Hz); 130,0; 130,3; 131,3; 132,0; 133,4; 138,5 (d, $J_{CP}$=9,0 Hz); 142,6 (d, $J_{CP}$=4,0 Hz); 142,8; 143,0; 143,0; 148,6 (d, $J_{CP}$=6,8 Hz); 151,0 (d, $J_{CP}$=3,4 Hz); 152,6 ppm.

6,6'-((4'-(tert-Butyl)-3-methoxy-5-methyl-[1,1'-biphenyl]-2,2'-diyl)bis(oxy))bis(9-(tert-butyl)-4-methoxy-2-methyldibenzo[d,f][3,2,1]dioxaphosphepine)

(5)

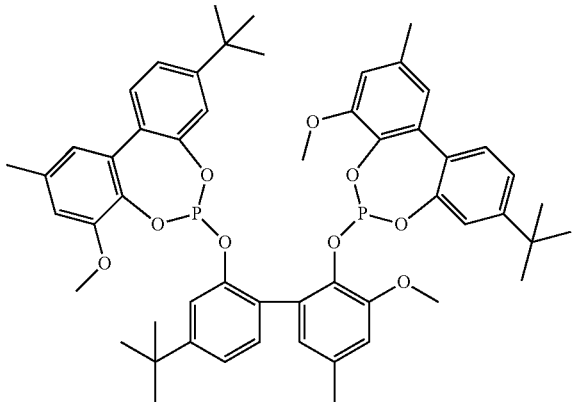

To a solution of 4'-(tert-butyl)-3-methoxy-5-methyl-[1,1'-biphenyl]-2,2'-diol (0.274 g; 0.957 mmol) in THF (10 ml) was added a solution of two equivalents of n-butyllithium in hexane (3.59 ml) at −20° C., the resulting mixture was stirred at this temperature for another 20 min and then a solution of 9-(tert-butyl)-6-chloro-4-methoxy-2-methyl-dibenzo[d,f][1,3,2]dioxaphosphepine (0.792 g; 2.258 mmol) in THF (11 ml) was added at room temperature. The reaction mixture was stirred overnight and the solvent was removed under reduced pressure. Toluene (25 ml) was added and the resulting suspension was filtered. The filtrate was filtered once again through silica gel and the solvent was removed under reduced pressure. The resulting solid was dried at 50° C./0.1 mbar for 3 h.

Yield: 0.856 g (0.936 mmol; 98%).

Elemental analysis (calc. for $CH_{54}H_{60}O_9P_2$=915.01 g/mol) C 70.67 (70.88); H 6.52 (6.61); P 6.69 (6.77) %.

$^{31}$P-NMR ($CD_2Cl_2$): 141,9 (d, $J_{PP}$=7.8 Hz); 142,2 (d, $J_{PP}$=7.8 Hz); 145,1 (d, $J_{PP}$=7.8 Hz); 145,2 (d, $J_{PP}$=7.8 Hz) ppm.

$^1$H-NMR ($CD_2Cl_2$): 1,22-1,33 (dd, 18 H); 1,37 (m, 9 H); 2,42 (m, 9 H); 3,81-3,88 (dd, 6 H); 4,02 (s, 3 H); 6,79-6,85 (m, 3 H, $H_{arom}$); 6,88 (m, 2 H, $H_{arom}$); 6,90-6,98 (m, 1 H, $H_{arom}$); 6,95 (m, 1 H, $H_{arom}$); 7,00-7,05 (m, 1 H, $H_{arom}$); 7,20-7,35 (m, 4 H, $H_{arom}$); 7,37-7,44 (m, 3 H, $H_{arom}$) ppm.

6,6'-((5'-Isopropyl-3-methoxy-4',5-dimethyl-[1,1'-biphenyl]-2,2'-diyl)bis(oxy))didibenzo[d,f][1,3,2]dioxaphosphepine

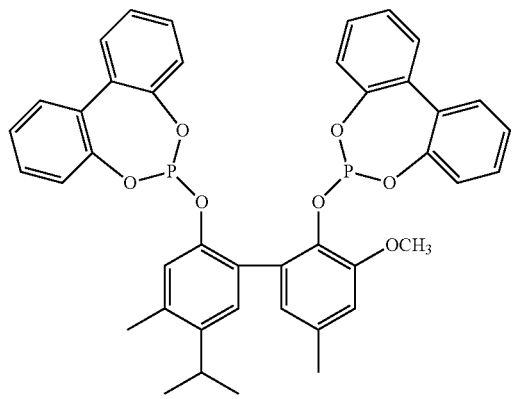

(6)

To a solution of 5'-isopropyl-3-methoxy-4',5-dimethyl-[1,1'-biphenyl]-2,2'-diol (0.485 g; 1.692 mmol) in toluene (12 ml) was added pyridine (0.385 g; 3.807 mmol), and the resulting mixture was added dropwise to a solution, cooled to 3° C., of 6-chlorodibenzo[d,f][1,3,2]dioxaphosphepine (0.933 g; 3.722 mmol) in toluene (12 ml). The reaction mixture was stirred overnight and then filtered. The filtrate was concentrated to dryness under reduced pressure and the resulting solid was dried at 50° C./0.1 mbar. The remaining substance was purified by column chromatography (hexane/toluene, 1:4, $R_f$=0.4).

Yield: 0.725 g (1.015 mmol; 60%).

Elemental analysis (calc. for $C_{42}H_{36}O_7P_2$=714.69 g/mol) C 70.77 (70.58); H 5.28 (4.98); P 8.85 (8.86) %.

$^{31}$P-NMR ($CD_2Cl_2$): 145,4 (d, $J_{PP}$=7,2 Hz); 148,2 (d, $J_{PP}$=7,2 Hz) ppm.

$^1$H-NMR ($CD_2Cl_2$): 1,24 (s, 3 H); 1,26 (s, 3 H); 2,43 (m, 3 H); 2,51 (m, 3 H); 3,22 (m, 1 H); 4,03 (s, 3 H); 6,72-6,83 (m, br, 3 H, $H_{arom}$); 6,95-6,99 (m, 2 H, $H_{arom}$); 6,99-7,02 (m, 1 H, $H_{arom}$); 7,13 (m, 1 H, $H_{arom}$); 7,22-7,33 (m, 9 H, $H_{arom}$); 7,42-7,50 (m, 4 H, $H_{arom}$) ppm.

$^{13}$C-NMR ($CD_2Cl_2$): 19,3; 21,5; 23,5; 29,4; 57,0; 113,8; 122,6 (d, $J_{CP}$=14,8 Hz); 124,8; 125,5 (d, $J_{CP}$=18,7 Hz); 128,3; 128,8; 129,4 (d, $J_{CP}$=14,5 Hz); 130,0 (d, $J_{CP}$=16,3 Hz); 131,5; 131,6; 134,3; 136,8; 137,9 (d, $J_{CP}$=6,3 Hz); 143,4; 147,5 (d, $J_{CP}$=8,2 Hz); 149,6 (d, $J_{CP}$=5,0 Hz); 149,7 (d, $J_{CP}$=4,5 Hz); 151,0 (d, $J_{CP}$=2,8 Hz) ppm.

2,2'-((5'-Isopropyl-3-methoxy-4',5-dimethyl-[1,1'-biphenyl]-2,2'-diyl)bis(oxy))bis(4,4,5,5-tetraphenyl-1,3,2-dioxapholane)

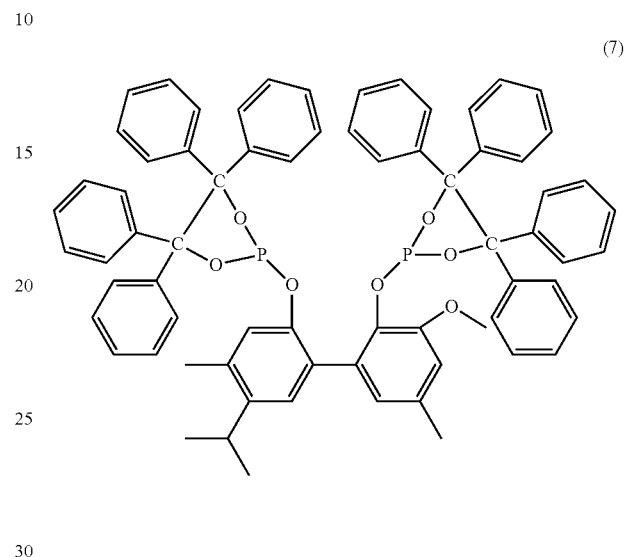

(7)

To a solution of 5'-isopropyl-3-methoxy-4',5-dimethyl-[1,1'-biphenyl]-2,2'-diol (0.330 g; 1.153 mmol) in THF (5 ml) were added 2 equivalents of n-butyllithium dissolved in hexane (4.3 ml) at −20° C. The mixture was stirred at −20° C. for 20 min and, after warming to room temperature, a solution of 2-chloro-4,4,5,5-tetraphenyl-1,3,2-dioxaphospholane (0.994 g; 2.307 mmol) in THF (8 ml) was added. The reaction mixture was stirred overnight and the solvent was removed under reduced pressure. Toluene (20 ml) was added and the resulting solution was filtered through silica gel. The filtrate was concentrated to dryness under reduced pressure. The resulting solid was dried at 50° C./0.1 mbar and then recrystallized from hot acetonitrile (12 ml). Yield: 0.782 g (0.728 mmol; 63%). Elemental analysis (calc. for $C_{70}H_{60}O_7P_2$=1075.19 g/mol) C 78.18 (78.20); H 5.69 (5.62); P 5.87 (5.76) %.

$^{31}$P-NMR ($CD_2Cl_2$): 139,3 (d, $J_{PP}$=9,1 Hz); 145,0 (d, $J_{PP}$=9,1 Hz) ppm.

$^1$H-NMR ($CD_2Cl_2$): 1,21 (m, 6 H); 2,27 (m, 3 H); 2,42 (m, 3 H); 3,96 (s, 3 H); 6,07 (m, 1 H, $H_{arom}$); 6,68 (m, 1 H, $H_{arom}$); 6,93 (m, 3 H, $H_{arom}$); 6,95-7,05 (m, 7 H, $H_{arom}$); 7,05-7,16 (m, 18 H, $H_{arom}$); 7,16-7,23 (m, 7 H, $H_{arom}$); 7,30-7,38 (m, 4 H, $H_{arom}$); 7,49-7,56 (m, 4 H, $H_{arom}$) ppm.

$^{13}$C-NMR ($CD_2Cl_2$): 19,1; 21,5; 23,5; 29,3; 57,5; 94,8 (d, $J_{CP}$=8,8 Hz); 95.5 (d, $J_{CP}$=8,2 Hz); 114,2; 123,3 (d, $J_{CP}$=10,0 Hz); 125,4; 127,1; 127,2; 127,3; 127,3; 127,4; 127,6; 128,3; 128,7 (d, $J_{CP}$=3,4 Hz); 129,0; 129,3; 129,9; 130,4 (m); 132,2 (d, $J_{CP}$=3,0 Hz); 133,5; 136,1; 138,5 (d, $J_{CP}$=6,8 Hz); 142,5; 142,7; 142,8; 143,0; 143,1 (d, $J_{CP}$=4,6 Hz); 146,1 (d, $J_{CP}$=5,2 Hz); 151,0 (d, $J_{CP}$=3,6 Hz) ppm.

6,6'-((3-Methoxy-5,5'-dimethyl-[1,1'-biphenyl]-2,2'-diyl)bis(oxy))didibenzo[d,f][1,3,2]dioxaphosphepine (8)

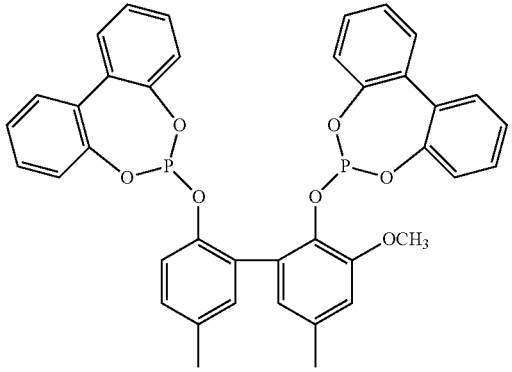

To a solution of 3-methoxy-5,5'-dimethyl-[1,1'-biphenyl]-2,2'-diol (0.419 g; 1.714 mmol) in toluene (12 ml) was added pyridine (0.390 g; 3.857 mmol), and the resulting mixture was added dropwise at 3° C. to a solution of 6-chlorodibenzo[d,f][1,3,2]dioxaphosphepine (0.945 g; 3.771 mmol) in toluene (12 ml). The reaction mixture was stirred overnight and then filtered. The filtrate was concentrated to dryness under reduced pressure and the resulting solid was dried at 50° C. The substance was dissolved in hot acetonitrile (25 ml). Crystallization was effected after the solution had been cooled and concentrated under reduced pressure to half its volume. Yield: 0.205 g (0.030 mmol; 18%).

Elemental analysis (calc. for $C_{39}H_{30}O_7P_2$=672.61 g/mol) C 69.58 (69.64); H 4.30 (4.49); P 9.25 (9.21) %.

$^{31}$P-NMR (CD$_2$Cl$_2$): 145,6 (d, $J_{PP}$=8,4 Hz); 148,2 (d, $J_{PP}$=8,4 Hz) ppm.

$^{1}$H-NMR (CD$_2$Cl$_2$): 42 (m, 6 H); 4,05 (s, 3 H); 6,75-6,82 (m, 3 H, H$_{arom}$); 6,95-7,02 (m, 3 H, H$_{arom}$); 7,17 (m, 1 H, H$_{arom}$); 7,24-7,36 (m, 10 H, H$_{arom}$); 7,42-7,50 (m, 4 H, H$_{arom}$) ppm.

$^{13}$C-NMR (CD$_2$Cl$_2$): 20,9; 21,4; 57,0; 113,9; 120,9 (d, $J_{CP}$=10,3 Hz); 122,6 (d, $J_{CP}$=11,6 Hz); 124,7; 125,5 (d, $J_{CP}$=19,2 Hz); 129,4 (d, $J_{CP}$=9,9 Hz); 129,8; 129,9; 130,1; 130,5 (d, $J_{CP}$=3,3 Hz); 131,2 (d, $J_{CP}$=3,0 Hz); 131,5 (m); 133,0; 134,3 (d, $J_{CP}$=4,6 Hz); 147,8 (d, $J_{CP}$=8,4 Hz); 149,4 (d, $J_{CP}$=5,0 Hz); 149,7 (d, $J_{CP}$=4,6 Hz); 151,0 (d, $J_{CP}$=2,9 Hz) ppm.

2,2'-((3-Methoxy-5,5'-dimethyl-[1,1'-biphenyl]-2,2'-diyl)bis(oxy)bis(4,4,5,5-tetraphenyl-1,3,2-dioxaphospholane)

(9)

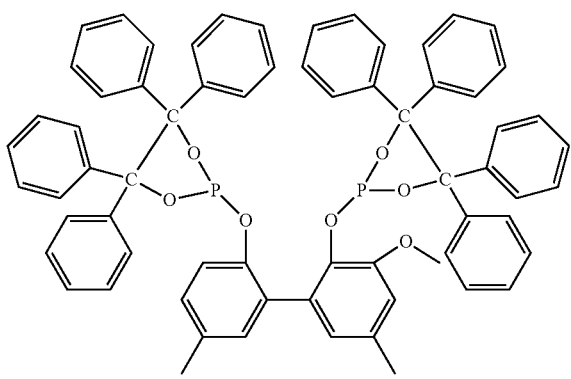

To a solution of 3-methoxy-5,5'-dimethyl-[1,1'-biphenyl]-2,2'-diol (0.241 g; 0.986 mmol) in THF (4 ml) were added 2 equivalents of n-butyllithium dissolved in hexane (3.7 ml) at −20° C. The mixture was first stirred at −20° C. for 20 min and, after warming to room temperature, a solution of 2-chloro-4,4,5,5-tetraphenyl-1,3,2-dioxaphospholane (0.850 g; 1.973 mmol) in THF (7 ml) was added. The reaction mixture was stirred overnight and the solvent was concentrated under reduced pressure. The residue was stirred with toluene (20 ml) and the resulting suspension was filtered through silica gel. The filtrate was concentrated to dryness under reduced pressure. The resulting solid was dried at 50° C./0.1 mbar and then recrystallized from hot acetonitrile (11 ml). The remaining substance was purified by column chromatography (hexane/toluene, 1:2, R$_f$=0.3). Yield: 0.430 g (0.416 mmol; 43%).

Elemental analysis (calc. for $C_{67}H_{54}O_7P_2$=1033.10 g/mol) C 77.64 (77.89); H 5.50 (5.27); P 6.05 (6.00) %.

$^{31}$P-NMR (CD$_2$Cl$_2$): 139,9 (d, $J_{PP}$=17,5 Hz); 145,1 (d, $J_{PP}$=17,5 Hz) ppm.

$^{1}$H-NMR (CD$_2$Cl$_2$): 26 (m, 3 H); 2,35 (m, 3 H); 3,91 (s, 3 H); 6,57 (m, 1 H, H$_{arom}$); 6,63 (m, 1 H, H$_{arom}$); 6,88 (m, 1 H, H$_{arom}$); 6,96 (m, 1 H, H$_{arom}$); 6,98-7,12 (m, 22 H, H$_{arom}$); 7,12-7,19 (m, 10 H, H$_{arom}$); 7,26-7,33 (m, 5 H, H$_{arom}$); 7,41-7,48 (m, 4 H, H$_{arom}$) ppm.

$^{13}$C-NMR (CD$_2$Cl$_2$): 20,9; 21,4; 57,4; 95,1 (d, $J_{CP}$=9,2 Hz); 95,5 (d, $J_{CP}$=8,8 Hz); 114,2; 121,4 (d, $J_{CP}$=10,0 Hz); 125,3; 127,2; 127,3; 127,3; 127,3; 127,4; 127,4; 127,5; 127,8; 128,3; 128,8; 129,1 (d, $J_{CP}$=3,2 Hz); 129,2 (d, $J_{CP}$=2,9 Hz); 129,5; 130,0; 130,3; 130,7 (d, $J_{CP}$=3,7 Hz); 131,7 (d, $J_{CP}$=3,3 Hz); 133,0; 133,5 (d, $J_{CP}$=14,0 Hz); 138,3 (d, $J_{CP}$=7,2 Hz); 142,7 (d, $J_{CP}$=4,3 Hz); 142,9; 143,0 (d, $J_{CP}$=4,6 Hz); 147,0 (d, $J_{CP}$=8,8 Hz); 151,1 (d, $J_{CP}$=2,9 Hz) ppm.

6,6'-((3-Methoxy-3',5,5'-trimethyl-[1,1'-biphenyl]-2,2'-diyl)bis(oxy))didibenzo[d,f][1,3,2]dioxaphosphepine (10)

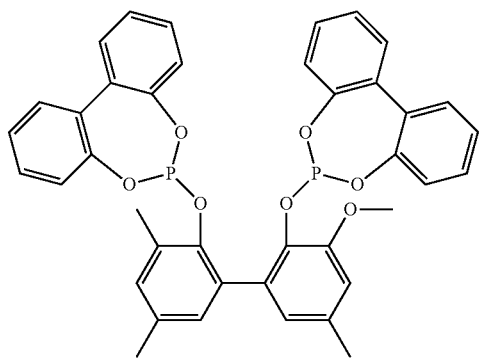

To a solution of 4',5-dimethoxy-6'-methyl-[1,1'-biphenyl]-2,3'-diol (0.361 g; 2.439 mmol) in toluene (8 ml) was added triethylamine (0.444 g; 4.385 mmol) and the mixture was cooled to 0° C. To this mixture was added dropwise a solution of 6-chlorodibenzo[d,f][1,3,2]dioxaphosphepine (0.57 g; 3.419 mmol) in toluene (13 ml). The reaction mixture was stirred at 0° C. for 45 min and at room temperature overnight and filtered through silica gel, and the filtrate was concentrated to dryness under reduced pressure.

Yield: 0.666 g (0.696 mmol; 69%). Elemental analysis (calc. for $C_{40}H_{32}O_7P_2$=686.16 g/mol): C 69.75 (69.97); H 4.76 (4.70); P 8.80 (9.02) %.

$^{31}$P-NMR (CD$_2$Cl$_2$): 142,4 (d, $J_{PP}$=9,7 Hz); 144.8 (d, $J_{PP}$=9,7 Hz); 146,7 (d, $J_{PP}$=13,6 Hz); 148,4 (d, $J_{PP}$=13,6 Hz) ppm. $^1$H-NMR (CD$_2$Cl$_2$): 2,01; 2,37; 2,41; 2,42; 2,46; 2,50 (6s, 9 H); 3,90; 4,04 (2s, 3 H); 6,76-7,63 (m, 20 H) ppm.

2,2'-((3-Methoxy-3',5,5'-trimethyl-[1,1'-biphenyl]-2, 2'-diyl)bis(oxy)bis(4,4,5,5-tetraphenyl-1,3,2-dioxa-phospholane)

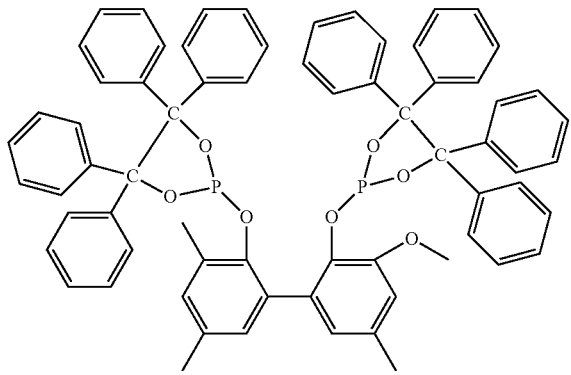

(11)

To a solution of 3-methoxy-3',5,5'-trimethyl-[1,1'-biphenyl]-2,2'-diol (0.320 g; 1.241 mmol) in THF (9 ml) were added two equivalents of n-butyllithium dissolved in hexane (5 ml) at −20° C. The mixture was stirred at −20° C. for 20 min and then a solution of 2-chloro-4,4,5,5-tetraphenyl-1,3, 2-dioxaphospholane (1.176 g; 2.729 mmol) in THF (6 ml) was added at room temperature. The reaction mixture was stirred overnight and the solvent was removed under reduced pressure. Toluene (20 ml) was added and the resulting suspension was filtered. The solvent was removed under reduced pressure. The resulting solid was dried at 50° C./0.1 mbar and then recrystallized from hexane (27 ml). Yield: 1.082 g (1.034 mmol; 83%).

Elemental analysis (calc. for $C_{68}H_{56}O_7P_2$=1047.13 g/mol) C 78.11 (78.00); H 5.38 (5.39); P 6.02 (5.92) %.

$^{31}$P-NMR (CD$_2$Cl$_2$): 143,4 (d, $J_{PP}$=27,2 Hz); 145,1 (d, $J_{PP}$=27,2 Hz) ppm.

$^1$H-NMR (CD$_2$Cl$_2$): 1,89 (m, 3 H); 2,26 (m, 3 H); 2,40 (m, 3 H); 3,95 (s, 3 H); 6,75 (m, 1 H, H$_{arom}$); 6,87 (m, 1 H, H$_{arom}$); 6,94 (m, 1 H, H$_{arom}$); 6,98 (m, 1 H, H$_{arom}$); 7,02-7,04 (m, 1 H, H$_{arom}$); 7,04-7,09 (m, 11 H, H$_{arom}$); 7,09-7,11 (m, 4 H, H$_{arom}$); 7,11-7,21 (m, 12H, H$_{arom}$); 7.21-7,26 (m, 3 H, H$_{arom}$); 7,26-7,36 (m, 5 H, H$_{arom}$); 7,40-7,57 (m, 4 H, H$_{arom}$) ppm.

$^{13}$C-NMR (CD$_2$Cl$_2$): 17,0; 21,0; 21,5; 57,2; 94,8; 114,0; 125,9; 127,3; 127,4; 127,6; 128,3; 128,9; 129,0; 129,1; 129,2; 129,4; 130,0; 130,2; 131,0; 131,2; 132,4 (m); 133,0; 133,6; 138,7 (d, $J_{CP}$=6,8 Hz); 142,6 (d, $J_{CP}$=4,0 Hz); 142,7 (m); 143,2; 146,5 (d, $J_{CP}$=7,7 Hz); 151,4 (d, $J_{CP}$=3,5 Hz) ppm.

6,6'-((3-Methoxy-4',5,5'-trimethyl-[1,1'-biphenyl]-2, 2'-diyl)bis(oxy))didibenzo[d,f][1,3,2]dioxaphosphep-ine

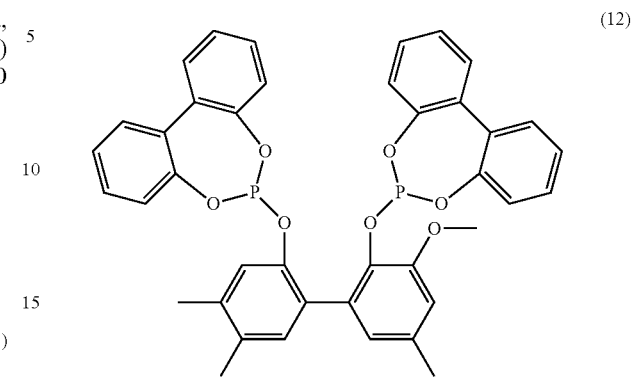

(12)

To a solution of 3-methoxy-4',5,5'-trimethyl-[1,1'-biphenyl]-2,2'-diol (0.334 g; 1.294 mmol) in toluene (7 ml) was added triethylamine (0.410 g; 4.048 mmol), the mixture was cooled to 0° C., and then added dropwise thereto was a solution of 6-chlorodibenzo[d,f][1,3,2]dioxaphosphepine (0.791 g; 3.157 mmol) in toluene (12 ml). The reaction mixture was stirred at 0° C. for 45 min and at room temperature for three days. The beige-yellow suspension was filtered and the resulting solid was washed with a little ice-cold toluene. The solid was taken up in 40 ml of toluene. The resulting suspension was stirred at 40° C. for 2 h and then filtered while warm. The filtrate was concentrated to dryness under reduced pressure and the residue was dried at 0.1 mbar. Yield: 0.254 g (0.370 mmol; 29%).

Elemental analysis (calc. for $C_{40}H_{32}O_7P_2$=686.60 g/mol) C 69.79 (69.97); H 4.81 (4.70); P 9.01 (9.02) %.

$^{31}$P-NMR (CD$_2$Cl$_2$): 145,6 (d, $J_{PP}$=8,4 Hz); 148.2 (d, $J_{PP}$=8,4 Hz) ppm.

$^1$H-NMR (CD$_2$Cl$_2$): 2,31 (m, 3 H); 2,42 (m, 3 H); 2,43 (m, 3 H); 4,03 (s, 3 H); 6,75-6,81 (m, 3 H, H$_{arom}$); 6,94-6,98 (m, 2 H, H$_{arom}$); 7,00 (m, 1 H, H$_{arom}$); 7,12 (m, 2 H, H$_{arom}$); 7,23-7,35 (m, 8 H, H$_{arom}$); 7,42-7,50 (m, 4 H, H$_{arom}$) ppm.

$^{13}$C-NMR (CD$_2$Cl$_2$): 19,2; 19,8; 21,4; 57,0; 113,7; 122,2 (d, $J_{CP}$=10,1 Hz); 122,5 (d, $J_{CP}$=13,1 Hz); 124,8; 125,3; 125,6; 125,6; 125,6; 127,9; (d, $J_{CP}$=3,4 Hz); 128,6; 129,2 (d, $J_{CP}$=15,5 Hz); 129,3; 129,8 (d, $J_{CP}$=16,6 Hz); 131,2; 131,5 (m); 133,0; 133,2; 134,3; 137,9; 138,1; 147,8 (d, $J_{CP}$=8,5 Hz); 149,5 (d, $J_{CP}$=4,9 Hz); 149,7 (d, $J_{CP}$=10,1 Hz); 150,9 (d, $J_{CP}$=2,8 Hz) ppm.

2,2'-((3-Methoxy-4',5,5'-trimethyl-[1,1'-biphenyl]-2, 2'-diyl)bis(oxy))bis(4,4,5,5-tetraphenyl-1,3,2-dioxa-phospholane)

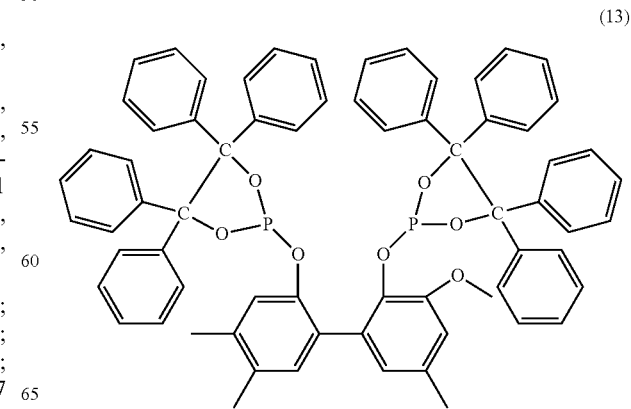

(13)

To a stirred solution of 3-methoxy-4',5,5'-trimethyl-[1,1'-biphenyl]-2,2'-diol (0.328 g; 1.268 mmol) in toluene (7 ml) was added triethylamine (0.402 g; 3.974 mmol). Added dropwise at 0° C. to the resulting mixture was a solution of 2-chloro-4,4,5,5-tetraphenyl-1,3,2-dioxaphospholane (1.202 g; 2.789 mmol) in toluene (10 ml), and the resulting mixture was stirred at 0° C. for another 45 min. Then the reaction mixture was stirred at room temperature for three days and then at 70° C. for 37 h. The mixture was filtered through silica gel, the filtrate was concentrated to dryness under reduced pressure and the resulting solid was dried at room temperature under reduced pressure for 2 h. Yield: 1.003 g (0.958 mmol; 76%).

Elemental analysis (calc. for $C_{68}H_{56}O_7P_2$=1047.07 g/mol) C 78.13 (78.00); H 5.41 (5.39); P 6.03 (5.92) %.

$^{31}$P-NMR (CD$_2$Cl$_2$): 139,7 (d, $J_{PP}$=15,6 Hz); 145,1 (d, $J_{PP}$=15,6 Hz) ppm.

$^1$H-NMR (CD$_2$Cl$_2$): 2,18 (s, 3 H); 2,22 (s, 3 H); 2,39 (s, 3 H) 3,95 (s, 3 H); 6,32 (s, 1 H, H$_{arom}$), 6,76 (br, 1 H, H$_{arom}$); 6,91 (br, 1 H, H$_{arom}$); 6,92 (s, 1 H, H$_{arom}$); 6,99-7,52 (m, 20 H, H$_{arom}$) ppm.

$^{13}$C-NMR (CD$_2$Cl$_2$): 19,0; 19,6; 21,4; 57,4; 95,0 (d, $J_{CP}$=8,8 Hz); 95,4 (d, $J_{CP}$=8,4 Hz); 114.0; 122,7 (d, $J_{CP}$=9,8 Hz); 125,4; 125,6; 127,0; 129,5; 130,0; 130,3; 131,5; 131,7; 131,9; 133,1; 133,4; 137,3; 138,3; 140,2 (d, $J_{CP}$=4,0 Hz); 141,0 (d, $J_{CP}$=5,3 Hz); 142,7 (d, $J_{CP}$=4,2 Hz); 142,9 (d, $J_{CP}$=5,8 Hz); 143,0 (d, $J_{CP}$=4,6 Hz); 146,7 (d, $J_{CP}$=7,2 Hz); 151,0 (d, $J_{CP}$=3,4 Hz) ppm.

6-((1-(3-(tert-Butyl)-2-dibenzo[d,f][1,3,2]dioxaphosphepin-6-yloxy)-5-methoxyphenyl)naphthalen-2-yl)oxy)dibenzo[d,f][1,3,2]dioxaphosphepine

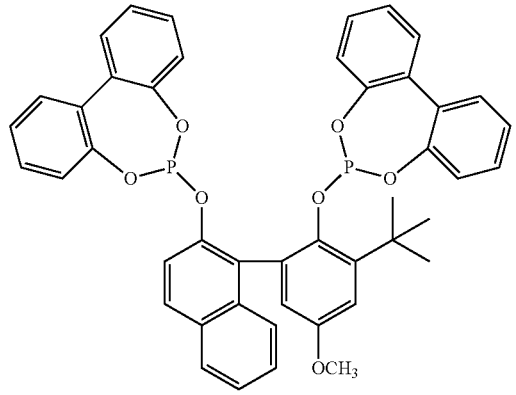

(14)

To a solution of 1-(3-(tert-butyl)-2-hydroxy-5-methoxyphenyl)naphthalen-2-ol (0.400 g; 1.240 mmol) in toluene (7 ml) was added triethylamine (0.524 g; 5.182 mmol) and the resulting mixture added dropwise at 0° C. to a solution of 6-chlorodibenzo[d,f][1,3,2]dioxaphosphepine (0.684 g; 2.728 mmol) in toluene (9 ml). The reaction mixture was stirred at 0° C. for 45 min and at room temperature overnight. The orange-yellow mixture was filtered through silica gel and the filtrate was concentrated to dryness under reduced pressure. The resulting solid was dried at 50° C./0.1 mbar for 3 h. Yield: 0.503 g (0.670 mmol; 65%).

Elemental analysis (calc. for $C_{45}H_{36}O_7P_2$=750.68 g/mol) C 71.94 (71.99); H 5.01 (4.83); P 8.33 (8.25) %.

$^{31}$P-NMR (CD$_2$Cl$_2$): 144,6 (d, $J_{PP}$=7,8 Hz); 145,9; 146,0; 146,4 (d, $J_{PP}$=7,8 Hz) ppm.

$^1$H-NMR (CD$_2$Cl$_2$): 1,47+1,60 (2s, 9 H); 3,80+3,82 (2s, 3 H); 6,29 (m, 1H, H$_{arom}$); 6,70 (m, 1H, H$_{arom}$): 6,77-8,10 (m, 22 H, H$_{arom}$) ppm.

$^{13}$C-NMR (CD$_2$Cl$_2$): 30,8; 31,3; 31,3; 35,7; 35,9; 56,0; 56,0; 114,7; 114,8; 114,9; 115,5; 121,0; 133,0; 134,8; 138,4; 142,0 (d, $J_{CP}$=2,2 Hz); 144,0; 144,2 (d, $J_{CP}$=2,8 Hz); 146,6 (d, $J_{CP}$=4,6 Hz); 148,8; 149,7; 149,9 (d, $J_{CP}$=2,5 Hz); 150,0 (d, $J_{CP}$=3,3 Hz); 155,9 (d, $J_{CP}$=4,0 Hz) ppm.

2-(2-(tert-Butyl)-4-methoxy-6-(2-(4,4,5,5-tetraphenyl-1,3,2-dioxaphospholan-2-yl)oxy)napthalen-1-yl)phenoxy)-4,4,5,5-tetraphenyl-1,3,2-dioxaphospholane

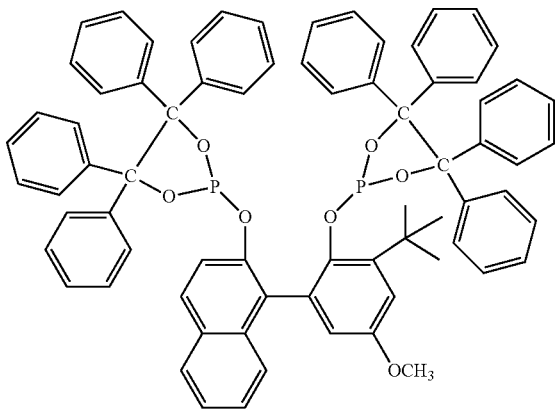

(15)

To a solution of 1-(3-(tert-butyl)-2-hydroxy-5-methoxyphenyl)naphthalen-2-ol (0.312 g; 0.969 mmol) in toluene (6 ml) was added triethylamine (0.307 g; 3.037 mmol) and the resulting mixture added dropwise at 0° C. to a solution of 2-chloro-4,4,5,5-tetraphenyl-1,3,2-dioxaphospholane (0.918 g; 2.131 mmol) in toluene (10 ml). The mixture was stirred at 0° C. for 45 min, at room temperature for 3 days and at 70° C. for 37 h. Then the mixture was filtered through silica gel. The filtrate was concentrated to dryness and the resulting solid was dried at room temperature and 0.1 mbar for 2 h. Yield: 0.891 g (0.802 mmol; 83%). The product holds 86% of the signal intensity in the $^{31}$P NMR spectrum. Attempted purification was unsuccessful.

Elemental analysis (calc. for $C_{73}H_{60}O_7P_2$=1111.151 g/mol): C 73.39 (78.90); H 5.94 (5.44); P 5.26 (5.58) %.

$^{31}$P-NMR (CD$_2$Cl$_2$): 140,5 (d, $J_{PP}$=35,0 Hz); 145,9 (d, $J_{PP}$=35,0 Hz) ppm.

$^1$H-NMR (CD$_2$Cl$_2$): 1,12 (s, 3H), 3,77 (s, 3H), 6,55-6,06 (m) ppm.

$^{13}$C-NMR (CD$_2$Cl$_2$): 30,4; 35,0; 94,2 (d, $J_{CP}$=7,9 Hz); 94,5 (d, $J_{CP}$=8,1 Hz); 114,1; 114,7; 121,9 (d, $J_{CP}$=11.5 Hz); 125,1; 126,9 (d, $J_{CP}$=6,3 Hz); 127,0 (d, $J_{CP}$=4,2 Hz); 127,1; 127,3; 127,4; 128,0; 128,3 (d, $J_{CP}$=3,7 Hz); 128,4 (d, $J_{CP}$=4,4 Hz); 128,7; 129,1; 129,6, 130,2; 130,4; 131,4; 142,6 (m); 155,5 ppm.

Procedure for the Catalysis Experiments

The hydroformylation was conducted in a 200 ml autoclave equipped with pressure-retaining valve, gas flow meter, sparging stirrer and pressure pipette from Premex Reactor AG, Lengau, Switzerland. To minimize the influence of moisture and oxygen, the toluene used as solvent was dried with sodium ketyl and distilled under argon. The following substrates used as substrate were heated at reflux over sodium and distilled under argon for several hours: 1-octene (Aldrich), cis/trans-2-pentene (Aldrich) and n-octenes (Oxeno GmbH, octene isomer mixture of 1-octene: ~3%; cis+trans-2-octene; ~49%; cis+trans-3-octene: ~29%; cis+trans-octene-4: ~16%; structurally isomeric octenes: ~3%).

For the experiments, the following solutions of rhodium in the form of [(acac)Rh(COD)] (acac=acetylacetonate anion; COD=1,5-cyclooctadiene) (OMG AG & Co. KG, Hanau, DE) as the catalyst precursor were introduced into the autoclave in toluene under an argon atmosphere: for experiments at 100 ppm by mass of rhodium 10 ml of a 4.31 millimolar solution, for 40 ppm by mass the same amount of an appropriately diluted solution. The appropriate amount of the phosphite compound, generally 2 to 5 ligand equivalents per unit rhodium, dissolved in toluene was then added. By adding further toluene (the total mass of toluene was determined for the GC analysis, see below), the starting volume of the catalyst solution was adjusted to a) 41.0 ml in the case of intended addition of 15 ml of the olefin via the pressure pipette (1-octene, n-octenes and experiments with elevated 2-pentene concentration), or b) 51.9 ml in the case of intended addition of 4.1 ml of 2-pentene. The mass of toluene introduced was determined in each case. Starting weights of the olefins: 1-octene (10.62 g; 94.64 mmol), n-octenes (10.70 g; 95.35 mmol), 2-pentene 9.75 g; 139.00 mmol. The autoclave was heated while stirring (1500 rpm) to the temperatures stated in each case at a total gas pressure (synthesis gas: Linde; $H_2$ (99.999%):CO (99.997%)=1:1) of a) 42 bar for a final pressure of 50 bar b) 12 bar for a final pressure of 20 bar and c) 7 bar for a final pressure of 10 bar. After reaching the reaction temperature, the synthesis gas pressure was increased to a) 48.5 bar for a final pressure of 50 bar, b) 19.5 bar for a final pressure of 20 bar and c) 9.5 bar for a final pressure of 10 bar and the olefin (mixture) specified in the table in each case was injected under a positive pressure of about 3 bar set in the pressure pipette. The reaction was conducted at a constant pressure of 50, 20 or 10 bar (closed-loop pressure controller from Bronkhorst, the Netherlands) over 4 h. After the reaction time had elapsed, the autoclave was cooled to room temperature, decompressed while stirring and purged with argon. 1 ml of each reaction mixture was removed immediately after the stirrer had been switched off, diluted with 5 ml of pentane and analysed by gas chromatography: HP 5890 Series II plus, PONA, 50 m×0.2 mm×0.5 µm. Residual olefin and aldehyde were determined quantitatively against the toluene solvent as internal standard.

Results of the Catalysis Experiments
Solvent: toluene
Yld.=yield
Sel.=selectivity
p=pressure in [bar]
T=temperature in [°C]
t=time in [h]
[Rh]=rhodium concentration in [ppm]
L/Rh=ratio of ligand to rhodium Comparative ligands selected were the ligands A and B. They were prepared according to DE 10 2006 058 682 A1.

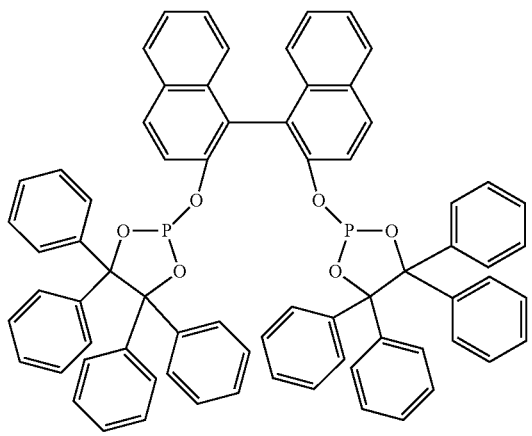

Ligand A

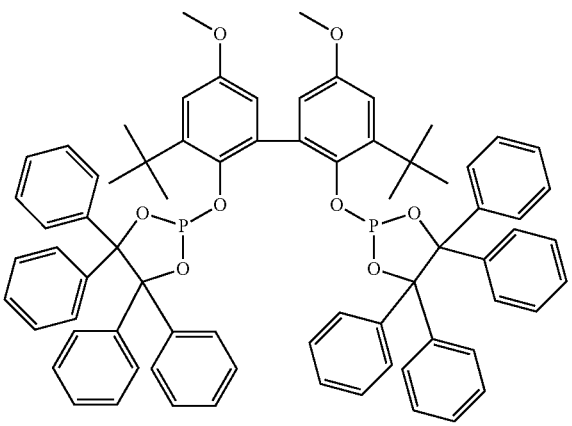

Ligand B

The inventive compounds are identified by *.

TABLE 1

| | | | 1-Octene | | | | |
|---|---|---|---|---|---|---|---|
| Ligand | p (bar) | T (° C.) | t (h) | [Rh] (ppm) | L/Rh | Yld. (%) | Sel. (%) |
| 1* | 50 | 100 | 4 | 40 | 2 | 92 | 93.1 |
| 2* | 50 | 100 | 4 | 40 | 2 | 91 | 90.5 |
| 3* | 50 | 100 | 4 | 40 | 2 | 90 | 90.0 |
| 4* | 50 | 100 | 4 | 40 | 2 | 93 | 90.7 |
| 5* | 50 | 100 | 4 | 40 | 2 | 91 | 87.3 |
| 6* | 50 | 100 | 4 | 40 | 2 | 91 | 90.8 |
| 7* | 50 | 100 | 4 | 40 | 2 | 92 | 87.3 |
| 8* | 50 | 100 | 4 | 40 | 2 | 93 | 90.2 |
| 9* | 50 | 100 | 4 | 40 | 2 | 92 | 91.5 |
| 10* | 50 | 100 | 4 | 40 | 2 | 91 | 91.7 |
| 11* | 50 | 100 | 4 | 40 | 2 | 89 | 95.1 |
| 12* | 50 | 100 | 4 | 40 | 2 | 93 | 90.4 |
| 13* | 50 | 100 | 4 | 40 | 2 | 97 | 73.9 |
| 14* | 50 | 100 | 4 | 40 | 2 | 91 | 89.6 |
| 15* | 50 | 100 | 4 | 40 | 2 | 89 | 95.9 |
| A | 50 | 100 | 4 | 40 | 2 | 89 | 83 |

As can be inferred from Table 1, the ligands are notable for very good yields in the hydroformylation of terminal olefins, more specifically 1-octene here. All inventive compounds have a yield at least as good as that of the comparative ligand A.

Compounds 11 and 15, which have the same yield as comparative ligand A, 89%, both have much better selectivity.

TABLE 2

| | | | 2-Pentene | | | | |
|---|---|---|---|---|---|---|---|
| Ligand | p (bar) | T (° C.) | t (h) | [Rh] (ppm) | L/Rh | Yld. (%) | Sel. (%) |
| 1* | 20 | 120 | 4 | 100 | 2 | 83 | 67.3 |
| 2* | 20 | 120 | 4 | 100 | 2 | 74 | 70.1 |
| 3* | 20 | 120 | 4 | 100 | 2 | 93 | 57.0 |
| 4* | 20 | 120 | 4 | 100 | 2 | 69 | 67.9 |
| 5* | 20 | 120 | 4 | 100 | 2 | 98 | 53.1 |
| 6* | 20 | 120 | 4 | 100 | 2 | 89 | 57.6 |
| 7* | 20 | 120 | 4 | 100 | 2 | 68 | 56.9 |
| 8* | 20 | 120 | 4 | 100 | 2 | 83 | 59.4 |
| 9* | 20 | 120 | 4 | 100 | 2 | 75 | 68.4 |
| 10* | 20 | 120 | 4 | 100 | 2 | 90 | 63.0 |
| 11* | 20 | 120 | 4 | 100 | 2 | 47 | 79.5 |
| 12* | 20 | 120 | 4 | 100 | 2 | 87 | 59.1 |
| 13* | 20 | 120 | 4 | 100 | 2 | 72 | 72.5 |
| 14* | 20 | 120 | 4 | 100 | 2 | 95 | 58.4 |
| 15* | 20 | 120 | 4 | 100 | 2 | 93 | 75.7 |
| B | 20 | 120 | 4 | 96 | 2 | 14 | 99 |

With comparative ligand B, a very good selectivity of 99% was achieved for 2-pentene, but the yield at 14% is so low that the use of such a ligand is only of little interest for an industrial scale process. The space-time yields with this ligand are so poor that this opposes the use of the comparative ligand B from an economic point of view.

The inventive compounds all have an acceptable to very good yield in combination with a good selectivity.

As the experimental results show, the stated object is achieved by the inventive compounds.

It has thus been possible for the first time to generate bisphosphites which contain an unsymmetric central biaryl unit, i.e. an unsymmetric backbone, and have good to very good hydroformylation properties. This was demonstrated by a multitude of examples. Such specific structures and ligands of this kind were entirely unknown and unobtainable to date. These bisphosphites have a novel kind of asymmetry. The special feature here is the asymmetry within the central biaryl unit, which leads to unsymmetric bisphosphites. These unsymmetric bisphosphites are thus structurally entirely different from the bisphosphites described in the prior art, in which unsymmetric bisphosphite ligands are generated via a particular arrangement of symmetric biaryl units, for example in that the two outer units differ, but the individual units (central unit and outer units) are symmetric per se.

The invention claimed is:

1. A compound having one of the four general structures I to IV:

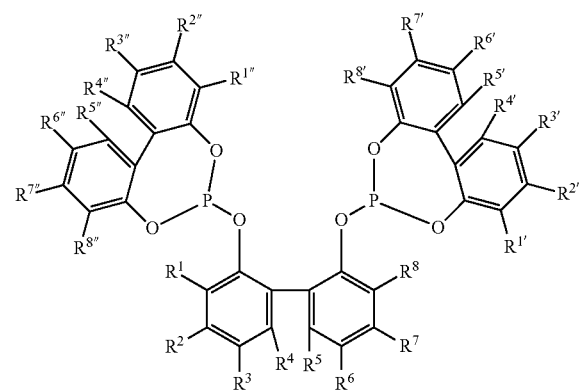

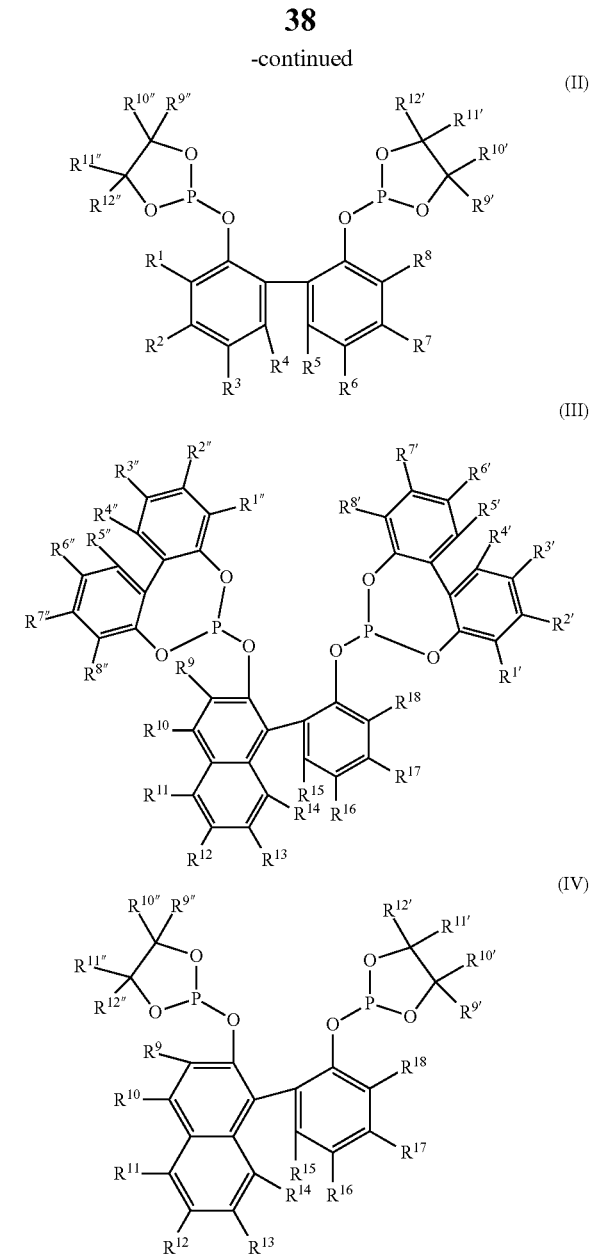

where
$R^1, R^2, R^3, R^4, R^5, R^6, R^7, R^8, R^9, R^{10}, R^{11}, R^{12}, R^{13}, R^{14}, R^{15}, R^{16}, R^{17}, R^{18}$ are selected from the group consisting of —H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —$SO_3H$, —CN, —$NH_2$, and —N[($C_1$-$C_{12}$)-alkyl]$_2$;

$R^{1'}, R^{2'}, R^{3'}, R^{4'}, R^{5'}, R^{6'}, R^{7'}, R^{8'}, R^{1''}, R^{2''}, R^{3''}, R^{4''}, R^{5''}, R^{6''}, R^{7''}, R^{8''}$ are selected from the group consisting of —H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —$SO_3H$, —$NH_2$, and —N[($C_1$-$C_{12}$)-alkyl]$_2$;

$R^{9'}, R^{10'}, R^{11'}, R^{12'}, R^{9''}, R^{10''}, R^{11''}, R^{12''}$ are selected from:

—H or —($C_6$-$C_{20}$)-aryl;

and the two radicals in at least two of the four following radical pairs are not the same radical: $R^1$ and $R^8$, $R^2$ and $R^7$, $R^3$ and $R^6$, $R^4$ and $R^5$;

where the alkyl and aryl groups mentioned may be substituted.

2. The compound according to claim 1, where the compound has the general structure (I).

3. The compound according to claim 1, where the compound has the general structure (II).

4. The compound according to claim 1, where the compound has the general structure (III).

5. The compound according to claim 1, where the compound has the general structure (IV).

6. The compound according to claim 1, where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ are selected from the group consisting of —H, —($C_1$-$C_{12}$)-alkyl, —O—($C_1$-$C_{12}$)-alkyl, —O—($C_6$-$C_{20}$)-aryl, —S-alkyl, and —S-aryl.

7. The compound according to claim 1, where $R^{1\prime}$, $R^{2\prime}$, $R^{3\prime}$, $R^{4\prime}$, $R^{5\prime}$, $R^{6\prime}$, $R^{7\prime}$, $R^{8\prime}$, $R^{1\prime\prime}$, $R^{2\prime\prime}$, $R^{3\prime\prime}$, $R^{4\prime\prime}$, $R^{5\prime\prime}$, $R^{6\prime\prime}$, $R^{7\prime\prime}$, $R^{8\prime\prime}$ are selected from the group consisting of —H, —($C_1$-$C_{12}$)-alkyl, —O—($C_1$-$C_{12}$)-alkyl, —O—($C_6$-$C_{20}$)-aryl, —S-alkyl, and —S-aryl.

8. The compound according to claim 1, where $R^{9\prime}$, $R^{10\prime}$, $R^{11\prime}$, $R^{12\prime}$, $R^{9\prime\prime}$, $R^{10\prime\prime}$, $R^{11\prime\prime}$, $R^{12\prime\prime}$ are each —($C_6$-$C_{20}$)-aryl.

9. The compound according to claim 1, where at least $R^1$ and $R^8$ are not the same radical.

10. The compound according to claim 1, where $R^{9\prime}$, $R^{10\prime}$, $R^{11\prime}$, $R^{12\prime}$, $R^{9\prime\prime}$, $R^{10\prime\prime}$, $R^{11\prime\prime}$, $R^{12\prime\prime}$ are each the same radical.

11. The compound according to claim 1, where the two radicals in at least one of the four following radical pairs are not the same radical: $R^{1\prime}$ and $R^{8\prime}$, $R^{2\prime}$ and $R^{7\prime}$, $R^{3\prime}$ and $R^{6\prime}$, $R^{4\prime}$ and $R^{5\prime}$, and the two radicals in at least one of the four following radical pairs are not the same radical: $R^{1\prime\prime}$ and $R^{8\prime\prime}$, $R^{2\prime\prime}$ and $R^{7\prime\prime}$, $R^{3\prime\prime}$ and $R^{6\prime\prime}$, $R^{4\prime\prime}$ and $R^{5\prime\prime}$.

12. The compound according to claim 1, where the two radicals in at least one of the four following radical pairs are not the same radical: $R^{1\prime}$ and $R^{8\prime}$, $R^{2\prime}$ and $R^{7\prime}$, $R^{3\prime}$ and $R^{6\prime}$, $R^{4\prime}$ and $R^{5\prime}$, and the two radicals in the four following radical pairs are the same radical: $R^{1\prime\prime}$ and $R^{8\prime\prime}$, $R^{2\prime\prime}$ and $R^{7\prime\prime}$, $R^{3\prime\prime}$ and $R^{6\prime\prime}$, $R^{4\prime\prime}$ and $R^{5\prime\prime}$.

13. A complex comprising:

a compound according to claim 1, a metal atom selected from the group consisting of Rh, Ru, Co, and Ir.

14. A method for catalysis of a hydroformylation reaction, comprising:

introducing the compound according to claim 1.

15. A process comprising the following process steps:

a) initially charging an olefin, b) adding a complex according to claim 13, or a compound having one of the four general structures I to IV:

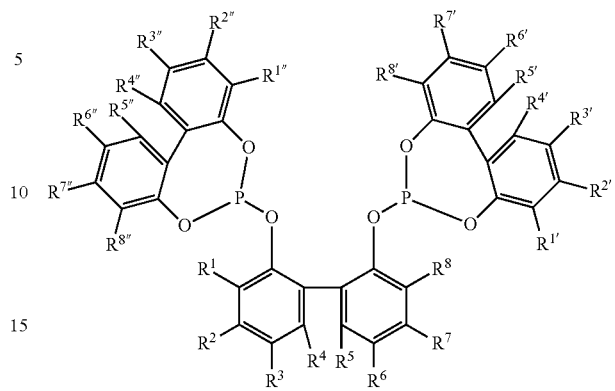
(I)

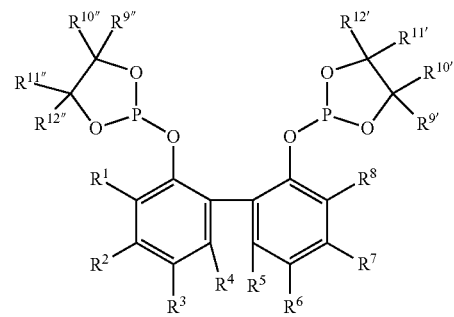
(II)

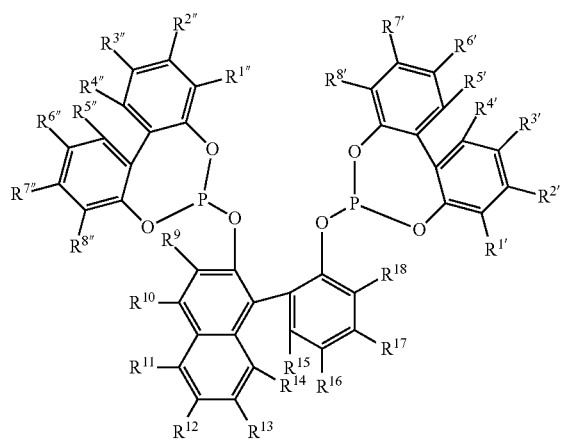
(III)

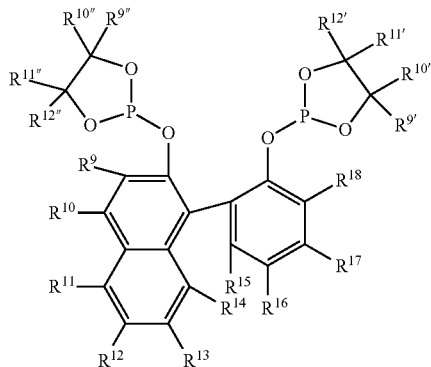
(IV)

where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ are selected from the group consist- ing of —H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —$SO_3H$, —CN, —$NH_2$, and —N[($C_1$-$C_{12}$)-alkyl]$_2$;

$R^{1\prime}$, $R^{2\prime}$, $R^{3\prime}$, $R^{4\prime}$, $R^{5\prime}$, $R^{6\prime}$, $R^{7\prime}$, $R^{8\prime}$, $R^{1\prime\prime}$, $R^{2\prime\prime}$, $R^{3\prime\prime}$, $R^{4\prime\prime}$, $R^{5\prime\prime}$, $R^{6\prime\prime}$, $R^{7\prime\prime}$, $R^{8\prime\prime}$ are selected from the group consisting of —H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —$SO_3H$, —$NH_2$, and —N[($C_1$-$C_{12}$)-alkyl]$_2$;

$R^{9\prime}$, $R^{10\prime}$, $R^{11\prime}$, $R^{12\prime}$, $R^{9\prime\prime}$, $R^{10\prime\prime}$, $R^{11\prime\prime}$, $R^{12\prime\prime}$ are selected from:

—H or —($C_6$-$C_{20}$)-aryl;

and the two radicals in at least two of the four following radical pairs are not the same radical: $R^1$ and $R^8$, $R^2$ and $R^7$, $R^3$ and $R^6$, $R^4$ and $R^5$;

where the alkyl and aryl groups mentioned may be substituted, and a substance including a metal atom selected from the group consisting of Rh, Ru, Co, and Ir, c) feeding in $H_2$ and CO, d) heating the reaction mixture, with conversion of the olefin to an aldehyde.

\* \* \* \* \*